(12) United States Patent
Eagan et al.

(10) Patent No.: US 11,787,758 B2
(45) Date of Patent: Oct. 17, 2023

(54) PROCESSES FOR PRODUCING ETHERS AND OLEFINS FROM PRIMARY ALCOHOLS

(71) Applicant: ExxonMobil Technology and Engineering Company, Annandale, NJ (US)

(72) Inventors: Nathaniel M. Eagan, Arlington, MA (US); Michael P. Lanci, Flemington, NJ (US); George W. Huber, Middleton, WI (US); Paolo Andres Cuello Penaloza, Madison, WI (US); J. Scott Buchanan, Flemington, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 0 days.

(21) Appl. No.: 17/325,707

(22) Filed: May 20, 2021

(65) Prior Publication Data
US 2021/0363085 A1    Nov. 25, 2021

Related U.S. Application Data

(60) Provisional application No. 63/027,545, filed on May 20, 2020.

(51) Int. Cl.
| | | |
|---|---|---|
| *C07C 41/09* | (2006.01) | |
| *C07C 29/34* | (2006.01) | |
| *C07C 1/24* | (2006.01) | |

(52) U.S. Cl.
CPC ............. *C07C 41/09* (2013.01); *C07C 1/24* (2013.01); *C07C 29/34* (2013.01)

(58) Field of Classification Search
CPC ............ C07C 41/09; C07C 1/24; C07C 29/34
See application file for complete search history.

(56) References Cited

U.S. PATENT DOCUMENTS

| 8,398,728 B2 * | 3/2013 | Ozer ..................... C07C 41/09 44/448 |
| 2009/0205246 A1 * | 8/2009 | Tsuchida ............... C07B 61/00 44/452 |
| 2011/0065814 A1 | 3/2011 | Matson et al. |
| 2014/0235901 A1 | 8/2014 | Gadewar et al. |
| 2016/0326075 A1 * | 11/2016 | Sanz Yague ............ C07C 29/34 |
| 2019/0031585 A1 | 1/2019 | Ramasamy et al. |

FOREIGN PATENT DOCUMENTS

WO    2008/069983 A2    6/2008

OTHER PUBLICATIONS

Eagan et al., "Chemistries and processes for the conversion of ethanol into middle-distillate fuels", Nat. Rev. Chem., vol. 3 (2019), pp. 223-249.
Eagan et al., "Catalytic synthesis of distillate-range ethers and olefins from ethanol through Guerbet coupling and etherification", Green Chem., vol. 21 (2019), pp. 3300-3318.
Galebach et al., "Supercritical methanol depolymerization and hydrodeoxygenation of maple wood and biomass-derived oxygenates into renewable alcohols in a continuous flow reactor", ACS Sustainable Chem. Eng., vol. 7 (2019), pp. 15361-15372.
Eagan et al., "Kinetic modeling of alcohol oligomerization over calcium hydroxyapatite", ACS Catalysis, vol. 10 (2020), pp. 2978-2989.
Galebach et al., "Production of alcohols from cellulose by supercritical methanol depolymerization and hydrodeoxygenation", ACS Sustainable Chem. Eng., vol. 6 (2018), pp. 4330-4344.
The International Search Report and Written Opinion of PCT/US2021/033377 dated Sep. 6, 2021.
The International Search Report and Written Opinion of PCT/US2021/033394 dated Sep. 7, 2021.
Eagan et al., "Catalytic synthesis of distillate-range ethers and olefins from ethanol through Guerbet coupling and etherification", Green Chemistry, vol. 1, No. 12, (2019), pp. 3300-3318.

* cited by examiner

*Primary Examiner* — Rosalynd A Keys
(74) *Attorney, Agent, or Firm* — SHOOK, HARDY & BACON, L.L.P.

(57) ABSTRACT

Provided are two-stage processes by which primary alcohols such as ethanol or 1-butanol are converted into distillate-range ethers and olefins utilizing Guerbet coupling followed by intermolecular dehydration. The ethers can be used, for example, as cetane-improvers in diesel fuel, while the olefins can be hydrogenated to afford paraffins.

25 Claims, 7 Drawing Sheets

PROCESSES FOR PRODUCING ETHERS AND OLEFINS FROM PRIMARY ALCOHOLS

CROSS-REFERENCE TO RELATED APPLICATIONS

This application is related to and claims the benefit of priority from U.S. Provisional Application No. 63/027,545 filed May 20, 2020, which is hereby incorporated by reference in its entirety.

FIELD OF THE INVENTION

This disclosure generally relates to processes for producing ethers and olefins from primary alcohols. In particular, the disclosure relates to processes for producing distillate range ethers and olefins, useful as components in liquid fuels, such as diesel and jet fuel.

BACKGROUND OF THE INVENTION

The production of distillate-range fuels from biomass-derived alcohols has recently received attention due to the projected increase in the demand of these fuels and the commercialization of alcohol production.

While ethanol production is commercially well established with over 25 billion barrels produced per year, its fuel applications are currently confined to gasoline with blending levels that have been historically limited to around 10 vol. % in the United States. However, the demand for gasoline is projected to decrease over the next few decades, while the demand for heavier $C_8$-$C_{22}$ distillate fuels, such as jet fuel and diesel is projected to increase.

Therefore, technologies for the conversion of ethanol into diesel and jet fuel blendstocks which can take advantage of the existing ethanol infrastructure are desirable.

Several approaches have been proposed for the conversion of ethanol to distillate fuels as recently discussed in Nat. Rev. Chem., 2019, 3, 223-249. However, the selective production of diesel blendstocks from ethanol with high cetane numbers (CNs), a measure of combustion quality, remains challenging.

The most common technologies involve acid-catalyzed ethanol dehydration to ethylene followed by olefin oligomerization with solid acids or transition metals. While dehydration and oligomerization can be performed in a single reactor when using acid catalysis, ethylene oligomerization is slow and necessitates operation at temperatures above 300° C. where the more highly reactive products (resulting from their increased substitution) can be rapidly converted through undesirable side-reactions including cracking, hydrogen transfer, and aromatization. As a result, such processes are limited to producing mainly C3-C8 paraffins and C6-C12 aromatics, species more suitable for use in gasoline or in the chemical industry (e.g. BTEX).

Alternatively, transition metals can be used to catalyze ethylene oligomerization selectively at lower temperatures. The olefins produced obey statistically-constrained Schulz-Flory distributions which limit ethylene to be at most 63 C % selective to the distillate range (C8-C22) and at most 51 C % selective to specifically the diesel range (C10-C22) in single-pass conversion. Typically, this oligomerization also involves homogeneous catalysts, organic solvents, and alkylating agents which require downstream separation processes.

Supported Ni and Co catalysts have shown promise as heterogeneous alternatives, though the same mechanisms lead to similar limitations.

To overcome the limitations of these two oligomerization chemistries, they can be combined in series such that transition metals are used to convert ethylene to C4-C6 olefin mixtures that can be oligomerized using solid acids without significant side-reactions. The latter stage promotes the formation of branched oligomers, which can be beneficial for cold flow properties, but detrimental to cetane number.

An alternative oligomerization chemistry which can be performed in a single step and introduces branching in a more predictable manner is Guerbet coupling. This coupling reaction formally involves three reactions performed in a single catalytic system: (1) dehydrogenation of two alcohols to aldehydes, (2) aldol condensation to an alkenal, and (3) hydrogenation to a saturated alcohol. The product alcohol can then undergo continued condensation reactions with another alcohol present in the system. United States Patent Application Publication No. 20190031585 describes a method and copper MgO—$Al_2O_3$ catalyst for converting ethanol to higher alcohols.

Ethers possess high cetane numbers and can be produced selectively from the acid-catalyzed etherification of linear primary alcohols.

Eagan et al have reported the synthesis of distillate-range ethers and olefins from ethanol through Guerbet coupling and etherification (Green Chem., 2019, 21, 3300-3318). A calcium hydroxyapatite catalyst was used to effect the Guerbet coupling.

Despite advances in the production of distillate range ethers and olefins from alcohols, there remains a need for improved processes. The present disclosure addresses, at least in part, this need.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

SUMMARY OF THE INVENTION

The present disclosure relates to processes for producing ethers and olefins from alcohols.

In one aspect the present disclosure provides a process for producing ethers and olefins from primary alcohols, said process comprising:
  (a) contacting a feed comprising primary alcohols with a first catalyst in a first reactor under conditions effective to produce an effluent comprising higher alcohols; and
  (b) contacting at least some of the higher alcohols produced in (a) with a second catalyst in a second reactor under conditions effective to dehydrate at least some of the higher alcohols to ethers and olefins.

In some embodiments, the primary alcohols in (a) comprise one or more C2 to C5 alcohols.

In some preferred embodiments, the primary alcohols comprise one or more of ethanol and 1-butanol.

In some embodiments, the contacting in step (a) is performed in the presence of one or more of hydrogen and inert gas.

In some embodiments, the higher alcohols produced in step (a) comprise one or more C4+ alcohols.

In some embodiments, step (a) is performed at a temperature from about 250° C. to about 370° C., preferably from about 280° C. to about 350° C., more preferably from about 300° C. to about 340° C.

In some embodiments the first catalyst is a heterogeneous catalyst comprising one or more Group A oxides, said Group A oxides being oxides of Mg, Ca, Zn, Mn, Sr, Si and Zr; one or more Group B oxides, said Group B oxides being one or more oxides of Al, La, Ga, Ce, Fe, Sc, Cr, P and V; and combinations of both Group A and Group B oxides, and, optionally, one or more of Cu, Ni, Pt, Pd, Rh, Co, Cs and Rb.

In some embodiments the first catalyst is a heterogeneous catalyst comprising one or more oxides of Mg, Ca, Zn, Sr, Al and Ce. In some embodiments the first catalyst comprises one of an oxide of Mg, Ca, Zn, Sr, Al and Ce.

In some embodiments the first catalyst is a heterogeneous catalyst comprising one or more oxides of Mg, Ca and Zn, one or more oxides of Al, La, Ga, Ce, Fe and Cr, and one or more of Cu, Ni, Pt, Pd, Rh and Co.

In some embodiments the first catalyst is a heterogeneous catalyst comprising one or more oxides of Mg, Ca and Sr, one or more of P and V, and, optionally, one or more of Cu, Ni, Pt, Pd, Rh and Co.

In some embodiments the first catalyst is a heterogeneous catalyst comprising Al and Si metal oxides and one or more of Cs and Rb.

The weight percent of the one or more of Cu, Ni, Pt, Pd, Rh and Co in the first catalyst may be up to about 10 wt. %, or from about 0.01 wt. % to about 9 wt. %, or from about 0.01 wt. % to about 8 wt. %, or from about 0.01 wt. % to about 7 wt. %, or from about 0.01 wt. % to about 6 wt. %, or from about 0.01 wt. % to about 5 wt. %, or from about 0.01 wt. % to about 4 wt. %, or from about 0.01 wt. % to about 3 wt. %, or from about 0.01 wt. % to about 2 wt. %, or from about 0.01 wt. % to about 1 wt. %, or from about 0.01 wt. % to about 0.5 wt. %, or from about 0.01 wt. % to about 0.4 wt. %, or from about 0.01 wt. % to about 0.3 wt. %, or from about 0.01 wt. % to about 0.2 wt. %, or from about 0.01 wt. % to about 0.1 wt. %, based on the total weight of the catalyst.

In some embodiments the first catalyst comprises Mg and Al oxides and Cu. The weight percent of Cu is preferably 0.05 wt. % to 1.0 wt. %, or 0.05 wt. % to 0.5 wt. %, or 0.05 wt. % to 0.2 wt. %, based on the total weight of the catalyst.

In some embodiments the first catalyst may be reduced prior to use.

In some embodiments, the yield of alcohols in step (a) is at least about 20%, or at least about 25%, or at least about 30%, or at least about 35%, or at least about 40%, or at least about 45%, or at least about 50%, or at least about 55%, or at least about 60%, or at least about 65%.

In some embodiments the selectivity to alcohols in step (a) is at least about 45%, or at least about 50%, or at least about 55%, or at least about 60%, or at least about 65%, or at least about 70%, or at least about 75%, or at least about 80%.

In some embodiments the selectivity to primary linear alcohols in step (a), based on total alcohols formed, is at least about 80%, or at least about 85%, or at least about 90%, or at least about 95%, or at least about 96%, or at least about 97%, or at least about 98%, or at least about 99%.

In some embodiments the selectivity to primary branched alcohols in step (a), based on total alcohols formed, is less than about 20%, or less than about 15%, or less than about 10%, or less than about 5%, or less than about 4%, or less than about 3%, or less than about 2%, or less than about 1%.

In some embodiments the effluent from step (a) further comprises one or more olefins.

In some embodiments the selectivity to olefins in step (a) is less than about 20%, or less than about 15%, or less than about 10%, or less than about 5%. The selectivity to olefins may be between about 0% and about 15%, or between about 0% and about 10%.

In some embodiments the effluent from step (a) further comprises one or more esters.

In some embodiments the selectivity to esters in step (a) is less than about 30%, or less than about 25%, or less than about 20%, or less than about 15%, or less than about 10% or less than about 5%. The selectivity to esters may be between about 1% and about 30%, or between about 2% and about 25%.

In some embodiments at least a portion of the esters formed in step (a) may be removed prior to contacting at least some of the higher alcohols produced in (a) with the second catalyst.

In some embodiments the effluent from step (a) further comprises one or more ethers.

In some embodiments the selectivity to ethers in step (a) is less than about 20%, or less than about 15%, or less than about 10%, or less than about 5%. The selectivity to ethers may be between about 0% and about 25%, or between about 0% and about 20%.

In some embodiments the effluent from step (a) further comprises one or more aldehydes and/or ketones.

In some embodiments the selectivity to aldehydes and ketones in step (a) is less than about 20%, or less than about 15%, or less than about 10%, or less than about 5%. The selectivity to aldehydes and ketones may be between about 0% and about 25%, or between about 0% and about 20%.

In some embodiments step (b) is performed at a temperature from about 100° C. to about 180° C.

Preferably, step (b) is performed in the absence of added solvent.

In some embodiments the second catalyst is a solid acid catalyst. Exemplary solid acid catalysts may comprise one or more of acidic resins, alumina and aluminosilicates, heteropoly acids, and tungsten and molybdenum functionalized oxides.

In some embodiments the ethers produced in step (b) comprise one or more C6-C20 ethers.

In some embodiments the olefins produced in step (b) comprise one or more C6-C14 olefins.

In another aspect the present disclosure provides a process for producing ethers and olefins from primary alcohols, said process comprising:

(a) contacting a feed comprising primary alcohols with a first catalyst in a first reactor under conditions effective to produce an effluent comprising higher alcohols and olefins;

(b) separating the effluent from step (a) into a first stream rich in olefins and one or more second streams rich in alcohols, wherein the one or more second streams rich in alcohols comprise a first stream rich in C2-C4 alcohols and a second stream rich in C4+ alcohols;

(c) recycling at least a portion of the first stream rich in C2-C4 alcohols to step (a);

(d) contacting at least a portion of the second stream rich in C4+ alcohols with a second catalyst in a second reactor under conditions effective to dehydrate at least some of the C4+ alcohols to ethers and olefins; and (e) separating the ethers and olefins produced in step (d) into a second stream rich in olefins, a stream rich in ethers, and a stream rich in alcohols.

In some embodiments, the primary alcohols comprise one or more C2 to C5 alcohols.

In some preferred embodiments, the primary alcohols in (a) comprise one or more of ethanol and 1-butanol.

In some embodiments, the contacting in step (a) is performed in the presence of one or more of hydrogen and inert gas.

In some embodiments, the higher alcohols produced in step (a) comprise one or more C4+ alcohols.

In some embodiments, step (a) is performed at a temperature from about 250° C. to about 370° C., preferably from about 280° C. to about 350° C., more preferably from about 300° C. to about 340° C.

In some embodiments the first catalyst is a heterogeneous catalyst comprising one or more Group A oxides, said Group A oxides being oxides of Mg, Ca, Zn, Mn, Sr, Si and Zr; one or more Group B oxides, said Group B oxides being one or more oxides of Al, La, Ga, Ce, Fe, Sc, Cr, P and V; and combinations of both Group A and Group B oxides, and, optionally, one or more of Cu, Ni, Pt, Pd, Rh, Co, Cs and Rb.

In some embodiments the first catalyst is a heterogeneous catalyst comprising one or more oxides of Mg, Ca, Zn, Sr, Al and Ce. In some embodiments the first catalyst comprises one of an oxide of Mg, Ca, Zn, Sr, Al and Ce.

In some embodiments the first catalyst is a heterogeneous catalyst comprising one or more oxides of Mg, Ca and Zn, one or more oxides of Al, La, Ga, Ce, Fe and Cr, and one or more of Cu, Ni, Pt, Pd, Rh and Co.

In some embodiments the first catalyst is a heterogeneous catalyst comprising one or more oxides of Mg, Ca and Sr, one or more of P and V, and, optionally, one or more of Cu, Ni, Pt, Pd, Rh and Co.

In some embodiments the first catalyst is a heterogeneous catalyst comprising Al and Si metal oxides and one or more of Cs and Rb.

The weight percent of the one or more of Cu, Ni, Pt, Pd, Rh and Co in the first catalyst may be up to about 10 wt. %, or from about 0.01 wt. % to about 9 wt. %, or from about 0.01 wt. % to about 8 wt. %, or from about 0.01 wt. % to about 7 wt. %, or from about 0.01 wt. % to about 6 wt. %, or from about 0.01 wt. % to about 5 wt. %, or from about 0.01 wt. % to about 4 wt. %, or from about 0.01 wt. % to about 3 wt. %, or from about 0.01 wt. % to about 2 wt. %, or from about 0.01 wt. % to about 1 wt. %, or from about 0.01 wt. % to about 0.5 wt. %, or from about 0.01 wt. % to about 0.4 wt. %, or from about 0.01 wt. % to about 0.3 wt. %, or from about 0.01 wt. % to about 0.2 wt. %, or from about 0.01 wt. % to about 0.1 wt. %, based on the total weight of the catalyst.

In some embodiments the first catalyst comprises Mg and Al oxides and Cu. The weight percent of Cu is preferably 0.05 wt. % to 1.0 wt. %, or 0.05 wt. % to 0.5 wt. %, or 0.05 wt. % to 0.2 wt. %, based on the total weight of the catalyst.

In some embodiments the first catalyst may be reduced prior to use.

In some embodiments, the yield of alcohols in step (a) is at least about 20%, or at least about 25%, or at least about 30%, or at least about 35%, or at least about 40%, or at least about 45%, or at least about 50%, or at least about 55%, or at least about 60%, or at least about 65%.

In some embodiments the selectivity to alcohols in step (a) is at least about 45%, or at least about 50%, or at least about 55%, or at least about 60%, or at least about 65%, or at least about 70%, or at least about 75%, or at least about 80%.

In some embodiments the selectivity to primary linear alcohols in step (a), based on total alcohols formed, is at least about 80%, or at least about 85%, or at least about 90%, or at least about 95%, or at least about 96%, or at least about 97%, or at least about 98%, or at least about 99%.

In some embodiments the selectivity to primary branched alcohols in step (a), based on total alcohols formed, is less than about 20%, or less than about 15%, or less than about 10%, or less than about 5%, or less than about 4%, or less than about 3%, or less than about 2%, or less than about 1%.

In some embodiments the selectivity to olefins in step (a) is less than about 20%, or less than about 15%, or less than about 10%, or less than about 5%. The selectivity to olefins may be between about 0% and about 15%, or between about 0% and about 10%.

In some embodiments the effluent from step (a) further comprises one or more esters.

In some embodiments the selectivity to esters in step (a) is less than about 30%, or less than about 25%, or less than about 20%, or less than about 15%, or less than about 10% or less than about 5%. The selectivity to esters may be between about 0% and about 30%, or between about 0% and about 25%.

In some embodiments the esters may comprise C6+ esters.

In some embodiments at least a portion of the esters formed in step (a) may be removed prior to contacting at least some of the higher alcohols produced in (a) with the second catalyst.

In some embodiments the effluent from step (a) further comprises one or more ethers.

In some embodiments the selectivity to ethers in step (a) is less than about 20%, or less than about 15%, or less than about 10%, or less than about 5%. The selectivity to ethers may be between about 0% and about 25%, or between about 0% and about 20%.

In some embodiments the effluent from step (a) further comprises one or more aldehydes and ketones.

In some embodiments the selectivity to aldehydes and ketones in step (a) is less than about 20%, or less than about 15%, or less than about 10%, or less than about 5%. The selectivity to aldehydes and ketones may be between about 0 and about 25%, or between about 0 and about 20%.

In some embodiments step (d) is performed at a temperature from about 100° C. to about 180° C.

Preferably, step (d) is performed in the absence of added solvent.

In some embodiments the second catalyst is a solid acid catalyst.

In some embodiments the ethers produced in step (d) comprise one or more C8-C24 ethers.

In some embodiments the olefins produced in step (d) comprise one or more C6-C14 olefins.

In some embodiments the process further comprises the step of combining at least a portion of the first stream rich in olefins produced in step (b) with at least a portion of the second stream rich in olefins produced in step (e).

Preferably, the first stream rich in olefins produced in step (b) comprises C2-C4 olefins.

In some embodiments the process further comprises the step of recycling at least a portion of the stream rich in alcohols produced in step (e) to step (d).

Preferably, the stream rich in ethers produced in step (e) comprises one or more C8-C16+ ethers.

Preferably, the second stream rich in olefins produced in step (e) comprises one or more C6+ olefins.

In some embodiments at least a portion of any one or more of the first stream rich in olefins, the second stream rich in olefins, and the combined streams of olefins, are oligomerized to higher olefins in the presence of a catalyst comprising acidic sites.

In some embodiments the catalyst comprising acid sites further comprises a transition metal, for example cobalt or nickel.

Preferably the higher olefins produced through oligomerization comprise C8-C16+ olefins.

In some embodiments at least a portion of the higher olefins are hydrotreated in the presence of a transition metal catalyst to paraffins.

Preferably the paraffins comprise C8-C16+ paraffins.

Further features and advantages of the present disclosure will be understood by reference to the following drawings and detailed description.

DETAILED DESCRIPTION OF THE EMBODIMENTS

Figure 1:
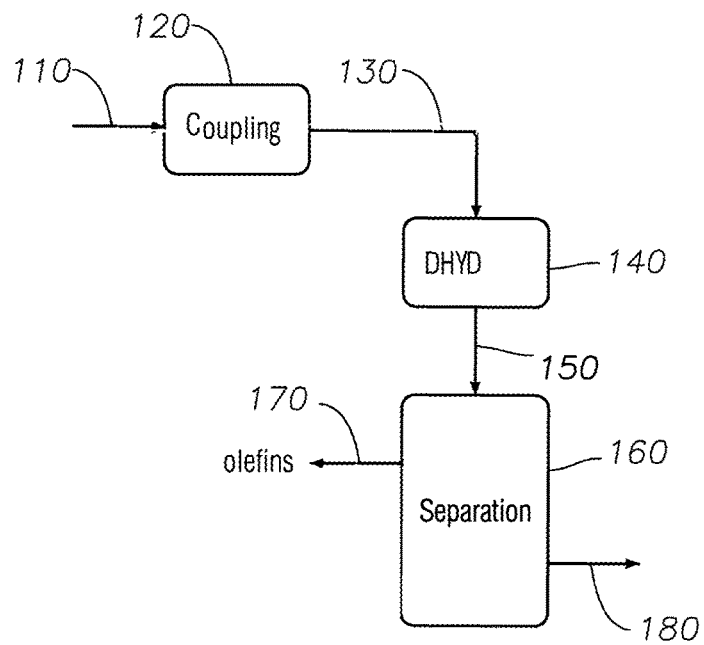
FIG. 1 is a flow diagram of a process for producing ethers and olefins from primary alcohols according to one embodiment of the present disclosure.

The following is a detailed description of the disclosure provided to aid those skilled in the art in practicing the present disclosure. Those of ordinary skill in the art may make modifications and variations in the embodiments described herein without departing from the spirit or scope of the present disclosure.

Although any methods and materials similar or equivalent to those described herein can also be used in the practice or testing of the present disclosure, the preferred methods and materials are now described.

It must also be noted that, as used in the specification and the appended claims, the singular forms 'a', 'an' and 'the' include plural referents unless otherwise specified. Thus, for example, reference to 'alcohol' may include more than one alcohols, and the like.

Throughout this specification, use of the terms 'comprises' or 'comprising' or grammatical variations thereon shall be taken to specify the presence of stated features, integers, steps or components but does not preclude the presence or addition of one or more other features, integers, steps, components or groups thereof not specifically mentioned.

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

Unless specifically stated or obvious from context, as used herein, the term "about" is understood as within a range of normal tolerance in the art, for example within two standard deviations of the mean. 'About' can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term 'about'.

Any processes provided herein can be combined with one or more of any of the other processes provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims.

The present disclosure relates to a two-stage process by which primary alcohols such as ethanol or 1-butanol are converted into distillate-range ethers and olefins utilizing Guerbet coupling followed by intermolecular dehydration. The ethers can be used, for example, as cetane-improvers in diesel fuel, while the olefins can be hydrogenated and blended with gasoline or oligomerized and hydrogenated to jet-range paraffins.

Embodiments of the herein disclosed processes utilize a first reaction in the presence of a heterogeneous catalyst to couple primary alcohols to higher alcohols. The higher alcohols may comprise mixtures of linear and branched alcohols. In a second reaction, the higher alcohols are dehydrated over a solid acid catalyst to olefins and ethers.

Primary Alcohol Coupling

In embodiments, a feed comprising primary alcohols are fed to a first reactor that contains a first catalyst.

In some embodiments, the primary alcohol coupling is performed in a single reactor, the reactor containing one or more beds of first catalyst.

The temperature of a catalyst bed may be from about 200° C. to about 500° C., preferably from about 250° C. to about 400° C., more preferably from about 280° C. to about 350° C.

The pressure in the reactor may be from about 15 psi (0.1 MPa) to about 1000 psi (6.9 MPa), or from about 100 psi (0.69 MPa) to about 1000 psi (6.9 MPa), or from about 200 psi (1.38 MPa) to about 500 psi (3.45 MPa).

In some embodiments, the partial pressure of hydrogen in the reactor is less than 100 psi (0.69 MPa), or less than 90 psi (0.62 MPa), or less than 80 psi (0.55 MPa) or less than 70 psi (0.48 MPa).

In some embodiments, the weight hour space velocity (WHSV) in the first reactor is from about 0.1 h$^{-1}$ to about 20 h$^{-1}$, or from about 0.1 h$^{-1}$ to about 10 h$^{-1}$, or from about 0.2 h$^{-1}$, to about 5 h$^{-1}$, or from about 0.5 h$^{-1}$ to about 5 h$^{-1}$.

In the present disclosure, yields are calculated on a carbon basis according to Equation (1) where $\dot{n}_{C,i}$ is the flow rate of carbon for species of category i.

$$Yield_i = Y_i = \frac{\dot{n}_{C,i,out}}{\dot{n}_{C,in}} \quad (1)$$

In some embodiments of the present disclosure, the yield of alcohols in the primary alcohol coupling reaction is at least about 20%, or at least about 25%, or at least about 30%, or at least about 35%, or at least about 40%, or at least about 45%, or at least about 50%, or at least about 55%, or at least about 60%, or at least about 65%.

At alcohol conversions below about 60%, conversion was calculated as the sum of all observed products according to Equation (2). This was performed since small changes in feed alcohol quantification can lead to large nonphysical fluctuations in the calculated conversion; carbon balances (carbon out divided by carbon in) ranged between 95 and 105 C %. The yield of unidentified gas chromatography (GC)-detected species was estimated by multiplying the unidentified GC area by the total yield of identified products divided by the total GC area of such products.

At elevated conversions where carbon balances are lower (85-95%), conversion was calculated based on the disappearance of the feed alcohol (Equation (3)) since Equation (2) does not account for undetected heavy species which are more likely to be present at these conversions.

$$Conversion = X = \sum Y_i \quad (2)$$

$$Conversion = X = \frac{\dot{n}_{C,feed\ alcohol\ in} - \dot{n}_{C,feed\ alcohol\ out}}{\dot{n}_{C,feed\ alcohol\ in}} \quad (3)$$

Selectivities are calculated on a carbon basis from the yield and the relevant metric for conversion based on Equation (4).

$$Selectivity_i = S_i = \frac{Y_i}{X} \quad (4)$$

In some embodiments of the present disclosure, the selectivity to alcohols in the alcohol coupling reaction is at least about 45%, or at least about 50%, or at least about 55%, or at least about 60%, or at least about 65%, or at least about 70%, or at least about 75%, or at least about 80%.

In other embodiments of the present disclosure, the selectivity to alcohols in the alcohol coupling reaction is between about 45% and about 80%, or between about 50% and about 75%.

In some embodiments of the present disclosure, the selectivity to primary linear alcohols in relation to all alcohols formed in the alcohol coupling step is at least about 80%, or at least about 85%, or at least about 90%, or at least about 95%, or at least about 96%, or at least about 97%, or at least about 98%, or at least about 99%.

In some embodiments, the selectivity to primary alcohols is between about 80% and about 99.5%.

A feature of the presently disclosed alcohol coupling reaction is the very high selectivity to primary linear alcohols in relation to all alcohols formed. In some embodiments, selectivities as high as 85% or greater are achieved at conversions of close to 70%.

In some embodiments the yield of primary linear alcohols is between about 10% and about 99%.

Typically, selectivity to primary linear alcohols, such as 1-butanol and 1-hexanol is very high at low conversions and can be as high as greater than 99%. As conversion is increased, selectivity to the primary linear alcohols decreases and the selectivity to primary branched alcohols, such as 2-ethyl-1-butanol and 2-ethyl-1-hexanol, increases. Advantageously, by controlling conversion, the ratio of primary linear alcohols to primary branched alcohols may be varied.

Alcohol Coupling Catalyst ('First Catalyst')

The first catalyst is a heterogeneous catalyst comprising one or more Group A oxides, said Group A oxides being oxides of Mg, Ca, Zn, Mn, Sr, Si and Zr; one or more Group B oxides, said Group B oxides being one or more oxides of Al, La, Ga, Ce, Fe, Sc, Cr, P and V; and combinations of both Group A and Group B oxides, and, optionally, one or more of Cu, Ni, Pt, Pd, Rh, Co, Cs and Rb.

The first catalyst may be a heterogeneous catalyst comprising one or more oxides of Mg, Ca, Zn, Sr, Al and Ce. In some embodiments the first catalyst comprises one of an oxide of Mg, Ca, Zn, Sr, Al and Ce.

The first catalyst may be a heterogeneous catalyst comprising one or more oxides of Mg, Ca and Zn, one or more oxides of Al, La, Ga, Ce, Fe and Cr, and one or more of Cu, Ni, Pt, Pd, Rh and Co.

The first catalyst may be a heterogeneous catalyst comprising one or more oxides of Mg, Ca and Sr, one or more of P and V, and, optionally, one or more of Cu, Ni, Pt, Pd, Rh and Co.

The first catalyst may be a heterogeneous catalyst comprising Al and Si metal oxides and one or more of Cs and Rb.

In some embodiments the weight percent of the one or more of Cu, Ni, Pt, Pd, Rh and Co in the first catalyst may be up to about 10 wt. %, or from about 0.01 wt. % to about 9 wt. %, or from about 0.01 wt. % to about 8 wt. %, or from about 0.01 wt. % to about 7 wt. %, or from about 0.01 wt. % to about 6 wt. %, or from about 0.01 wt. % to about 5 wt. %, or from about 0.01 wt. % to about 4 wt. %, or from about 0.01 wt. % to about 3 wt. %, or from about 0.01 wt. % to about 2 wt. %, or from about 0.01 wt. % to about 1 wt. %, or from about 0.01 wt. % to about 0.5 wt. %, or from about 0.01 wt. % to about 0.4 wt. %, or from about 0.01 wt. % to about 0.3 wt. %, or from about 0.01 wt. % to about 0.2 wt. %, or from about 0.01 wt. % to about 0.1 wt. %, based on the total weight of the catalyst.

In some embodiments the first catalyst comprises Mg and Al oxides and Cu. In some embodiments, the weight percent of Cu is preferably 0.01 wt. % to 0.2 wt. % based on the total weight of the catalyst.

Generally, a first catalyst having the desired activity can have a molar ratio of one or more of Mg, Ca, Zn, Mn, Sr, Si and Zr to one or more of Al, La, Ga, Ce, Fe, Sc, Cr, 0 and V of about 10 to about 1, for example about 5 to about 1, about 4 to about 1, or about 3 to about 1. In some embodiments, the molar ratio of one or more of Mg, Ca, and Zn to one or more of Al, La, and Ga, can be at least about 10, for example at least about 5, at least about 4, or at least about 3. Additionally, or alternately, the molar ratio of one or more of Mg, Ca, and Zn, to one or more of Al, La, and Ga can be about 10 or less, for example about 5 or less, about 4 or less, or about 3 or less.

In some preferred embodiments, the molar ratio of Mg to Al, can be at least about 5, for example at least about 4 or at least about 3. In such embodiments, the molar ratio of Mg to Al can optionally be about 5 or less, for example about 4 or less, or about 3 or less.

Preferably, the first catalyst is reduced prior to use. The first catalyst may be reduced through treatment with hydrogen at elevated temperature. Typical temperatures may be in the range 250° C. to 450° C., between 300° C. and 400° C.

Catalyst Form

First catalysts as described herein can employ the catalyst in a powder form, prepared, for example, by co-precipitation techniques or wet impregnation techniques, such as incipient wetness impregnation. Alternately, or additionally, the powder can be formulated into catalyst particles, such as by extrusion. Such catalyst particles, or extrudates, may be bound using one or more binders typically employed in the art.

Reactor Types

Various types of reactors may provide a suitable configuration for performing alcohol coupling. Suitable reactors may include fixed bed reactors, moving bed reactors, and slurry bed reactors. In some preferred embodiments the reactor is a fixed bed reactor.

It is noted that the activity and/or selectivity of a catalyst for alcohol coupling may vary as the catalyst is exposed to increasing amounts of primary alcohol.

In embodiments where a catalyst can be removed from the reactor for regeneration and recycle during operation of the reactor, such as a moving bed reactor, catalyst can be removed and replaced with regenerated catalyst.

In embodiments where fixed bed reactors are utilized, the reactors may comprise one or more beds of catalyst powder, particles or extrudates. Each bed may comprise the same catalyst, or, alternately, beds may comprise different catalysts. Where different catalysts are utilized, they may vary in terms of one or more of metal loading, metal type and basic metal oxide type.

For example, in one embodiment, a given reactor may contain more than one catalyst bed, each of which contain the same, for example, CuMgAl oxide catalyst. In another embodiment, a given reactor may contain more than one catalyst bed, wherein at least one bed has a different catalyst to another bed. For example one bed may contain a CuMgAl oxide having a particular Cu loading and another bed may contain a CuMgAl oxide catalyst having a different Cu loading. In another embodiment, one bed may contain, for example, a CuMgAl oxide catalyst and another bed may contain a different catalyst.

Alcohol Dehydration

In embodiments the higher alcohols formed through alcohol coupling are contacted with a second catalyst in a second reactor to dehydrate the higher alcohols to ethers and olefins.

In some embodiments, the dehydration is performed in a single reactor, the reactor containing one or more beds of second catalyst.

The temperature of a catalyst bed may be from about 100° C. to about 200° C., or from about 120° C. to about 180° C., or from about 130° C. to about 170° C., or from about 135° C. to about 165° C.

In some embodiments, the weight hour space velocity (WHSV) in the second reactor is from about 0.1 h$^{-1}$ to about 10 h$^{-1}$, or from about 0.2 h$^{-1}$ to about 5 h$^{-1}$, or from about 0.5 h$^{-1}$ to about 5 h$^{-1}$.

Dehydration Catalyst ('Second Catalyst')

In some embodiments the second catalyst is a solid acid catalyst. Exemplary solid acid catalysts may comprise one or more of acidic resins, alumina and aluminosilicates, heteropoly acids, and tungsten and molybdenum functionalized oxides.

Non-limiting examples of acidic resins include resins available under the trade names Amberlyst™, Nafion™ and Dowex™.

Suitable examples of Amberlyst™ resins include Amberlyst™ 15, 16, 31, 35, 39, 70 and 121. Suitable examples of Nafion™ resins include Nafion™ H and NR-50. Suitable examples of Dowex™ resins include Dowex™ 50W×2, 50W×4 and 50W×8.

Non-limiting examples of aluminosilicates include $SiO_2$—$Al_2O_3$, and zeolites such as H-β, H—Y, and H-ZSM-5.

Non-limiting examples of heteropoly acids include tungstophosphoric acid, silicotungstic acid, molybdotungstic acid, and molybdophosphoric acid, Non-limiting examples of tungsten and molybdenum functionalized oxides include $WO_x/ZrO_2$, $WO_x/TiO_2$, $WO_x/Al_2O_3$, $MoO_x/ZrO_2$, $MoO_x/TiO_2$, and $MoO_x/Al_2O_3$, wherein x is 1-3.

Model Alcohol Dehydrations

Experiments were performed individually on the major alcohols observed in the alcohol coupling step, namely the primary linear alcohols 1-butanol and 1-hexanol. These alcohols were dehydrated to di-n-butyl ether and di-n-hexyl ether respectively at about 97% selectivity. The only other products observed were olefins. This established that primary linear alcohols were dehydrated to ethers with high selectivity with only small amounts of olefins formed.

Dehydrations were also performed on the primary branched alcohols 2-ethyl-1-butanol and 2-ethyl-1-hexanol, which are formed in increasing amounts in the alcohol coupling step as conversion increases. On dehydration, these alcohols are more selective to olefins than the linear alcohols. 2-ethyl-1-butanol was about 65% selective to 3-methylpentenes and 2-ethyl-1-hexanol about 75% selective to 3-methylheptenes.

Dehydration of mixed alcohol feeds was examined under controlled reactant ratios to establish whether crossed products were formed. Mixtures of 1-butanol and 2-ethyl-1-hexanol were examined with molar ratios of 8:1, 2:1, 1:1, and 1:2.

Feeds with higher 1-butanol contents show higher ether selectivities and lower olefin selectivities. No species other than light olefins and ethers were observed. The conversion of a 1:1 molar ratio of 1-butanol and 2-ethyl-1-hexanol led to an ether selectivity of 59% and an olefin selectivity of 33% at 66% feed conversion. The conversion of 1-butanol was 79% while that of 2-ethyl-1-hexanol was lower at 59%. The cross-etherification product 1-butoxy-2-ethylhexane was positively identified via GC-MS-EI, clearly showing that cross-etherification occurred between linear and branched alcohols.

Model alcohol mixtures representative of ethanol coupled products from the alcohol coupling step were prepared and subjected to dehydration. Mixtures containing 1-butanol, 1-hexanol, 2-ethyl-1-butanol and 2-ethyl-1-hexanol were prepared having linear:branched ratios of 12.5, 5.3, 3.2 and 2.0.

The mixtures reacted to 65.0-69.5% conversion with ether selectivities ranging from 65.0-81.8%. Cross-etherification was observed between the various alcohols with ethers positively identified based on molecular weight via GC-MS-FI. As in the etherification of butanol-ethylhexanol mixtures, ether and olefin selectivities could be directly correlated with the linear:branched alcohol feed ratio, though ether selectivities were slightly lower than with the two-component feed. This implies that performing Guerbet condensation at higher conversions where the linear:branched alcohol ratio is lower will result in lower ether selectivities, though these ethers will be larger and therefore possess higher energy densities. The olefins were almost entirely 3-methylpentenes and 3-methylheptenes derived from the branched alcohols. These could be partially hydrogenated and utilized in gasoline or oligomerized with solid acids and hydrogenated to jet-range paraffins.

Combined Alcohol Coupling and Dehydration

After validation of the individual reaction stages, the two were combined in series to produce a mixture of distillate-range ethers from ethanol. In one embodiment ethanol condensation was first carried out at 42% conversion using a hydroxyapatite catalyst to produce C4+ alcohols at 82% selectivity. The product distribution remained steady for over 400 h time-on-stream.

Water is known to inhibit dehydration reactions and therefore is advantageously removed from the coupling products prior to dehydration. In some embodiments, molecular sieves may be used to reduce the water content of the ethanol derived alcohol mixture from, for example, 15 wt. % to less than, for example, 0.5 wt. %.

In some embodiments, unreacted ethanol may be removed via distillation since dehydration reactions involving ethanol would produce significant amounts of volatile C4-C6 ethers. The major components after ethanol removal are, for example, 1-butanol (about 50 wt. %), 2-ethyl-1-butanol (about 15 wt. %), 1-hexanol (about 12 wt. %), and 2-ethyl-1-hexanol (about 4 wt. %). In some embodiments, about 80 mol. % of the alcohols in this mixture are linear.

The alcohol mixture may then be converted to ethers over, for example, a solid acid catalyst, with, in some embodiments, about 75% alcohol conversion, about 70% ether selectivity, and about 10% olefin selectivity. This demonstrates that combination of the two catalytic steps in series necessitates only conventional separation processes already common in alcohol purification (i.e. distillation and drying with molecular sieves).

Assuming ethanol coupling is performed at, for example about 50% conversion with about 77% selectivity to alcohols, in some embodiments the product may then be separated into four streams: water, ethanol, olefins, and C4+ alcohols with other heavy by-products. The ethanol may be recycled to the alcohol coupling reactor. The alcohols and heavy by-products may be fed to a dehydration reactor. The selectivities of the dehydration process are directly linked to the ratio of linear:branched alcohols in the dehydration feed. The product stream from the dehydration reactor may be separated into four streams: olefins, ethers, water, and by-products.

In some embodiments, the olefins may be suitable for gasoline blending after partial hydrogenation. Alternatively, or additionally, the olefins may be combined with the olefins produced during alcohol coupling into a stream which may be oligomerized via acid or metal catalysis and then hydrogenated to jet-range paraffins.

In some embodiments, oligomerization may be 80% selective to the distillate range since oligomerization of C4-rich streams is selective to this range and the subsequent hydrogenation is well-established to be a highly selective process.

In some embodiments, the overall process demonstrates about a 60% yield of diesel-range ethers and about a 15% yield of jet-range paraffins with an overall about 75% distillate fuel yield from ethanol.

To understand the sensitivity of these yields to the conversion at which the alcohol coupling reactor is operated, correlations can be drawn between ethanol conversion and alcohol selectivity, olefin selectivity, and the linear:branched alcohol ratio. These can then be combined with correlations between the dehydration feed composition and product selectivities to predict overall process yields as a function of alcohol coupling conversion.

For example, in one embodiment, increasing ethanol conversion from about 10 to about 60% shifts overall ether yields from about 77 to about 59% while olefin yields increase from about 5 to about 16%, with total distillate yields of about 82 to about 75%. Combined with the maximum theoretical ethanol yield achievable from glucose fermentation (67% carbon basis), this technology may be used to produce distillate fuel from sugars at yields of, some embodiments, 50-55%.

While only conventional separation schemes are likely required in the herein disclosed processes (e.g. distillation, adsorption with molecular sieves, liquid-liquid extraction), the person of ordinary skill in the art would appreciate that these separations may be performed in a multitude of ways depending on how the process is designed. For example, removal of water from ethanol condensation products may only require molecular sieves if condensation is performed at low conversions. Operation at higher conversions may require both distillation and molecular sieves. Operation at yet higher conversions would additionally allow for the production of a biphasic product, thus water removal would only occur after C4+ organic products are removed via decantation. Such a phase separation may also be induced via the recycling of a heavy phase if this improved process economics.

Compared to conventional ethanol-to-distillate technologies, the herein disclosed process possesses several benefits. The C8+ ethers have much higher cetane than the products from acid-catalyzed olefin oligomerization. These ethers also have lower freezing points than linear paraffins of the same carbon number that can be produced through metal-catalyzed olefin oligomerization (followed by hydrogenation). The freezing points of dodecane and hexadecane, for example, are −10 and 18° C., respectively, while those of di-n-hexyl ether and di-n-octyl ether are −43 and −8° C., respectively. The herein disclosed process additionally uses solely inexpensive heterogeneous catalysts and does not require added solvents.

Process Embodiments

Referring first to FIG. 1, the process flow diagram illustrates the production of olefins and ethers from alcohols according to one embodiment of the present disclosure.

In a first step, primary alcohols are fed via line (110) to reactor (120) which contains one or more beds of heterogeneous catalyst. The effluent from the reactor, which comprises higher alcohols, is fed via line (130) to reactor (140) which contains one or more beds of heterogeneous dehydration catalyst. The effluent from reactor (140), which comprises olefins and ethers, is fed via line (150) to separation unit (160) which separates the olefins and ethers into olefin rich stream (170) and ether rich stream (180).

Figure 2:
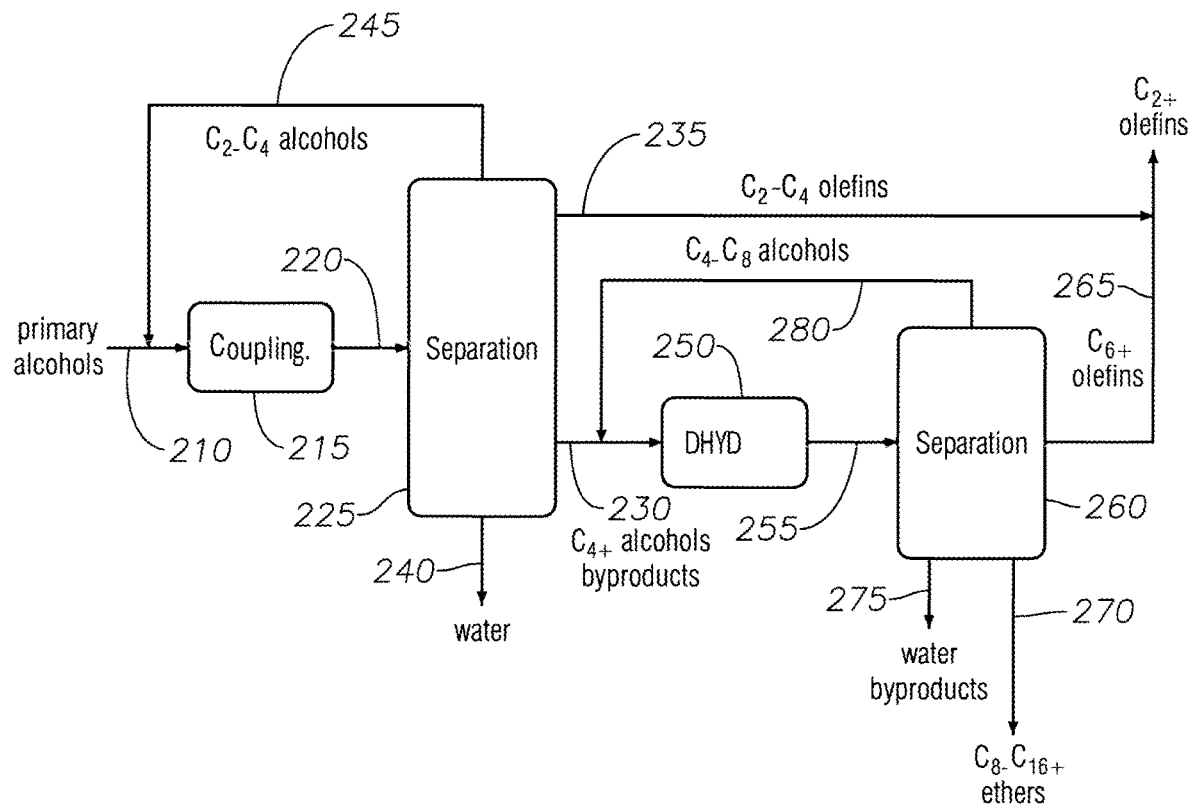
FIG. 2 is a flow diagram of a process for producing ethers and olefins from primary alcohols according to another embodiment of the present disclosure.

Referring to FIG. 2, the process flow diagram illustrates the production of olefins and ethers from alcohols according to another embodiment of the present disclosure.

In a first step, primary alcohols are fed via line (210) to reactor (215) which contains one or more beds of heterogeneous catalyst. The effluent from the reactor, which comprises higher alcohols, is fed via line (220) to separation unit (225) which separates the effluent into four streams. Stream (245) comprises light alcohols, for example in the $C_2$-$C_4$ range; stream (235) comprises olefins, for example in the $C_2$-$C_4$ range; stream (230) comprises heavier alcohols, for example greater than $C_4$; and stream (240) comprises water.

The light alcohol stream (245) is recycled to reactor (215) to build higher chain length compounds. The heavier alcohol stream (230) is fed to dehydration reactor (250) the effluent from which is fed via line (255) to separation unit (260) which separates the effluent into four streams.

Stream (280) comprises unreacted alcohols which are recycled back to the dehydration reactor feed (230); stream (265) comprises olefins, for example greater than $C_6$, the stream is combined with olefin stream (235) from separation (225); stream (270) comprises ethers, for example $C_8$-$C_{16+}$ ethers; and stream (275) comprises water and by-products.

Figure 3:
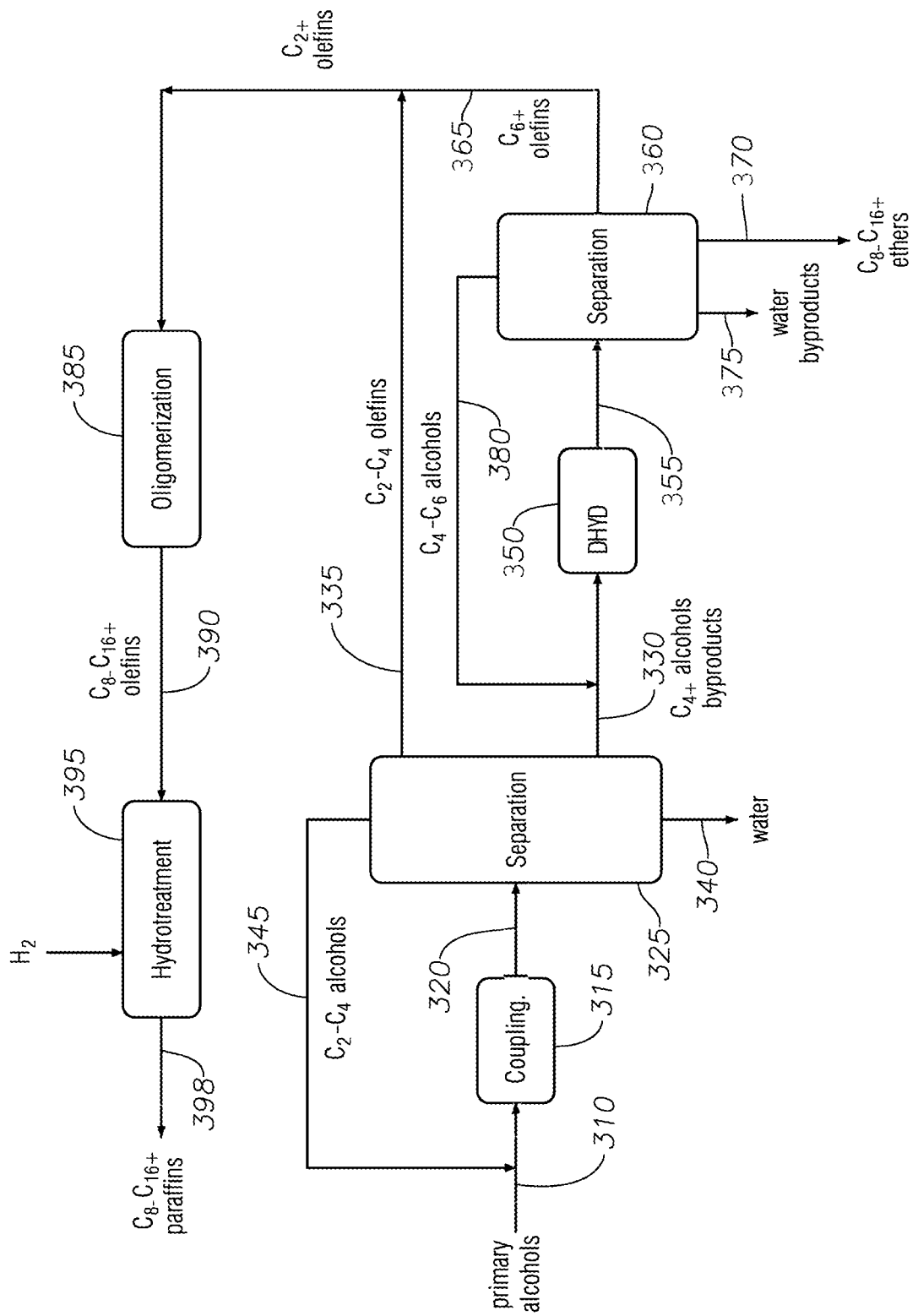
FIG. 3 is a flow diagram of a process for producing distillate range hydrocarbons and ethers from primary alcohols according to another embodiment of the present disclosure.

FIG. 3 illustrates a process flow diagram similar to that of FIG. 2, with the addition that combined olefin streams (335) and (365) are fed to reactor (385) which contains one or more beds of an olefin oligomerization catalyst. The effluent from this reactor, which contains higher olefins, for example in the range $C_8$-$C_{16+}$, is fed via line (390) to reactor (395) which contains one or more beds of a hydrotreating catalyst. Hydrogen is also fed to the reactor, resulting in effluent stream (398) which comprises higher paraffins, for example in the range $C_8$-$C_{16+}$.

EXAMPLES

Example 1: Alcohol Coupling Catalyst Preparation

A CuMgAl oxide catalyst was prepared by co-precipitation techniques. Three aqueous solutions were prepared as outlined in Tables 1 through 3.

TABLE 1

| Compounds and amounts for solution 1 | |
|---|---|
| Compound | Amount (g) |
| $Mg(NO_3)_2 \cdot 6H_2O$ | 35.51 |
| $Al(NO_3)_2 \cdot 9H_2O$ | 15.02 |
| $Cu(NO_3)_2 \cdot 3H_2O$ | 0.067 |
| $H_2O$ | 240.0 |

TABLE 2

| Compounds and amounts for solution 2 | |
|---|---|
| Compound | Amount (g) |
| $Na_2CO_3$ | 4.24 |
| $H_2O$ | 300 |

TABLE 3

| Compounds and amounts for solution 3 | |
|---|---|
| Compound | Amount (g) |
| NaOH | 16.0 |
| $H_2O$ | 400 |

The amounts of magnesium, aluminum and copper precursors were such that the molar ratios were Cu/Al=0.0072 and Mg/Al=3.46. The nominal copper loading was 0.1 wt. %. Solution 1 was added to solution 2 which was at a temperature of 60° C., while adding solution 3 to maintain a pH of 9-11 (a pH meter was typically used to ensure this). On NaOH addition and mixing, a precipitate formed which was then aged for 20 hours at 60° C. The precipitate was isolated by filtration and washed with a solution of 25.44 g Na2CO3 in 240 g water and then at least three times with 60° C. deionized water. The catalyst was dried overnight at 60° C. and then calcined in air at 600° C. for 2 hours with 4° C./min temperature increase. The yield of catalyst was typically about 7 g. The catalyst was sized between 35-100 mesh sieves (range may vary). The catalyst was reduced in a flow of $H_2$ at ambient pressure and 350° C. prior to use.

Example 2: Coupling of Ethanol to Higher Alcohols

Continuous gas phase coupling of ethanol was performed in a fixed bed reactor containing 4.32 g CuMgAl oxide catalyst powder as prepared in Example 1.

The temperature in the reactor was 325° C. and the total pressure 300 psi (2.1 MPa). Ethanol flow was adjusted to 0.134 and 0.600 mL/min to give WHSV, respectively, of 1.47 and 6.58 $h^{-1}$. $H_2$ flow was adjusted to fix $P_{Ethanol}$:$P_{H2}$ to a value of 4 (17.4 and 78 mL/min for, respectively, 1.47 and 6.58 $h^{-1}$). The partial pressure of $H_2$ was 60 psi (0.41 MPa).

Table 4 shows conversion and yields to products obtained in the tests.

TABLE 4

| WHSV ($h^{-1}$) | 6.58 | 1.47 |
|---|---|---|
| Contact time (s $kg_{cat}$/mol) | 25.2 | 113.1 |
| Conversion (%) | 54.63 | 67.92 |
| Alcohol | 33.84 | 39.32 |
| Primary linear alcohol | 30.49 | 34.63 |
| Primary branched alcohols | 2.47 | 3.25 |
| Secondary alcohols | 0.43 | 0.96 |
| Methanol | 0.45 | 0.48 |
| Aldehyde | 6.50 | 6.99 |
| Ketone | 1.43 | 2.61 |
| Ester | 9.23 | 15.11 |
| Ether | 0.21 | 0.68 |
| Paraffin | 0.11 | 0.15 |
| Olefin | 0.26 | 0.38 |
| Aromatic | 0.00 | 0.00 |
| Unidentified | 3.04 | 2.68 |

As WHSV increased and contact time decreased, ethanol conversion decreased. Alcohols were the major product, but at higher conversion (ca. 68%), increasing amounts of esters, aldehydes and olefins were produced. It is envisaged that at lower conversions, yields of alcohols would be even higher.

Table 5 shows the selectivity to products obtained in the tests.

TABLE 5

| | | |
|---|---|---|
| WHSV (h$^{-1}$) | 6.58 | 1.47 |
| Contact time (s kg$_{cat}$/mol) | 25.2 | 113.1 |
| Conversion (%) | 54.63 | 67.92 |
| Alcohol | 61.95 | 57.91 |
| Primary linear alcohol | 55.82 | 50.37 |
| Primary branched alcohols | 4.53 | 5.42 |
| Secondary alcohols | 0.78 | 1.42 |
| Methanol | 0.83 | 0.70 |
| Aldehyde | 11.90 | 10.29 |
| Ketone | 2.61 | 3.94 |
| WHSV (h$^{-1}$) | 6.58 | 1.47 |
| Contact time (s kg$_{cat}$/mol) | 25.2 | 113.1 |
| Conversion (%) | 54.63 | 67.92 |
| Ester | 16.90 | 22.23 |
| Ether | 0.38 | 1.00 |
| Paraffin | 0.21 | 0.22 |
| Olefin | 0.48 | 0.56 |
| Aromatic | 0.00 | 0.00 |
| Unidentified | 5.57 | 3.93 |

At the lower conversion, the fraction of primary linear alcohols relative to all alcohols was high. As conversion increased, increasing amounts of primary branched alcohols were produced.

Figure 4:
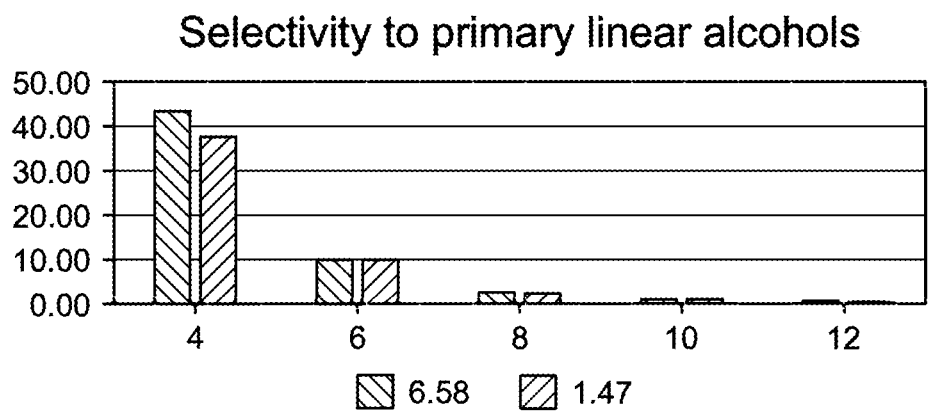
FIG. 4 is a bar chart showing selectivity to primary linear alcohols at different weight hour space velocities.

FIG. 4 illustrates the selectivity to primary linear alcohols based on carbon number and at different WHSV. Only even carbon numbered primary linear alcohols were produced, and 1-butanol and 1-hexanol were the only primary linear alcohols observed. As residence time increased, slightly increasing amounts of higher primary linear alcohols were observed.

Figure 5:
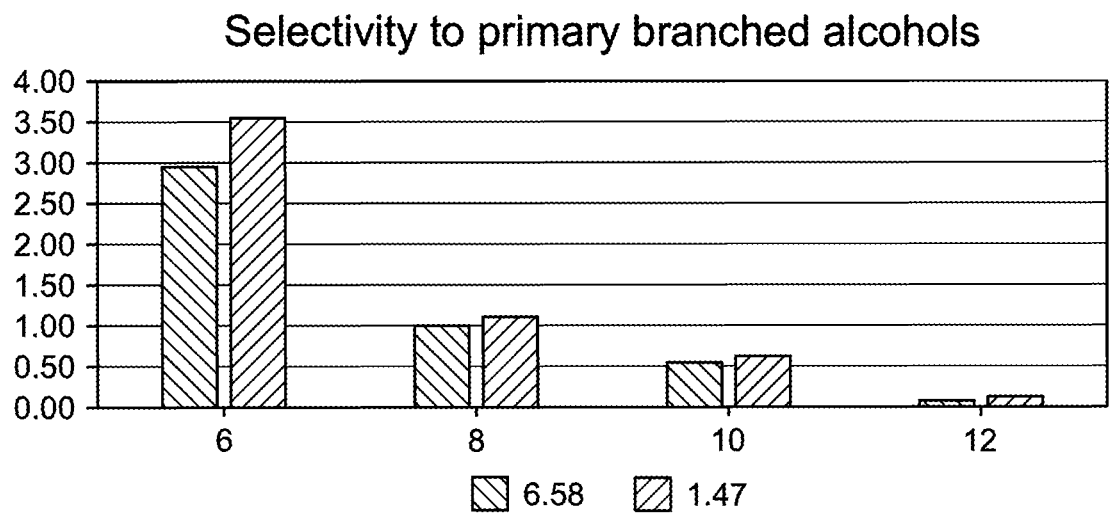
FIG. 5 is a bar chart showing selectivity to primary branched alcohols at different weight hour space velocities.

FIG. 5 illustrates the selectivity to primary branched alcohols based on carbon number and at different residence times. Only even carbon numbered primary branched alcohols were produced. As residence time increased, increasing amounts of higher primary branched alcohols were observed.

Figure 6:
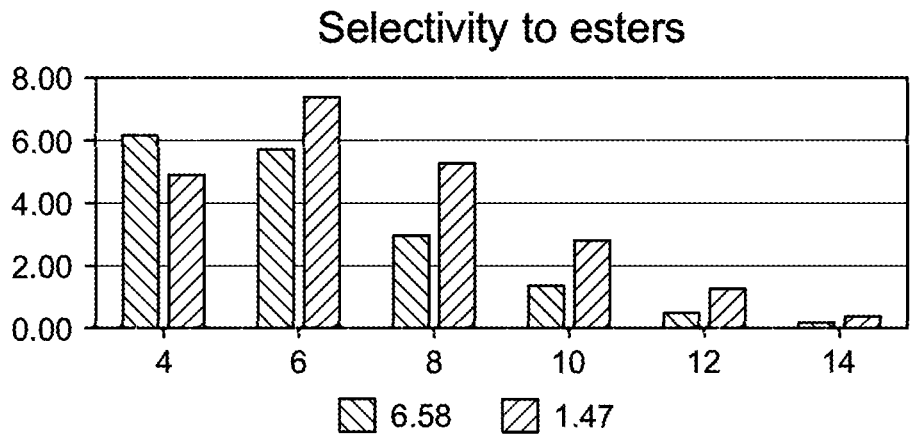
FIG. 6 is a bar chart showing selectivity to esters at different weight hour space velocities.

FIG. 6 illustrates the selectivity to esters based on carbon number and at different residence times. As residence time increased, increasing amounts of esters were observed, particularly C6+ esters.

Example 3: General Method for Alcohol Dehydration

Dehydration reactions were performed in a 45 mL Parr batch reactor with a 2.22 cm stir rod. Solid acid catalyst Amberlyst™ 70 was crushed and sieved to <177 µm and dried at 110° C. prior to reaction. In a typical reaction, 15 g of feed were first added to the reactor along with 750 mg of Amberlyst™ 70. The reactor was then sealed and pressurized with argon to about 290 psi (2 MPa) stirring at 750 rpm. The temperature was then increased to 150° C. with a ramp time of ~10 minutes prior to a 24 h hold. After 24 h the reactor was immediately submerged in an ice bath and cooled to <15° C. to minimize loss of volatile components.

After depressurization, the liquid products and catalyst were collected. The reactor and reactor head were then thoroughly rinsed (~75 mL total) with 1,4-dioxane to ensure full product collection. The resulting solution was then mixed and filtered through a 0.22 µm syringe filter. This solution was then further diluted in dioxane (20:1 by volume), and 1-pentanol was added as an internal standard prior to analysis. The solution was analyzed by gas chromatography (GC).

Example 4: Dehydration of Single-Component Alcohol Feeds

Following the method of Example 3, dehydrations were performed individually on the major alcohols observed in the alcohol coupling step, namely the primary linear alcohols 1-butanol and 1-hexanol. These alcohols were dehydrated to di-n-butyl ether and di-n-hexyl ether respectively at about 97% selectivity. The only other products observed were olefins.

Figure 7:
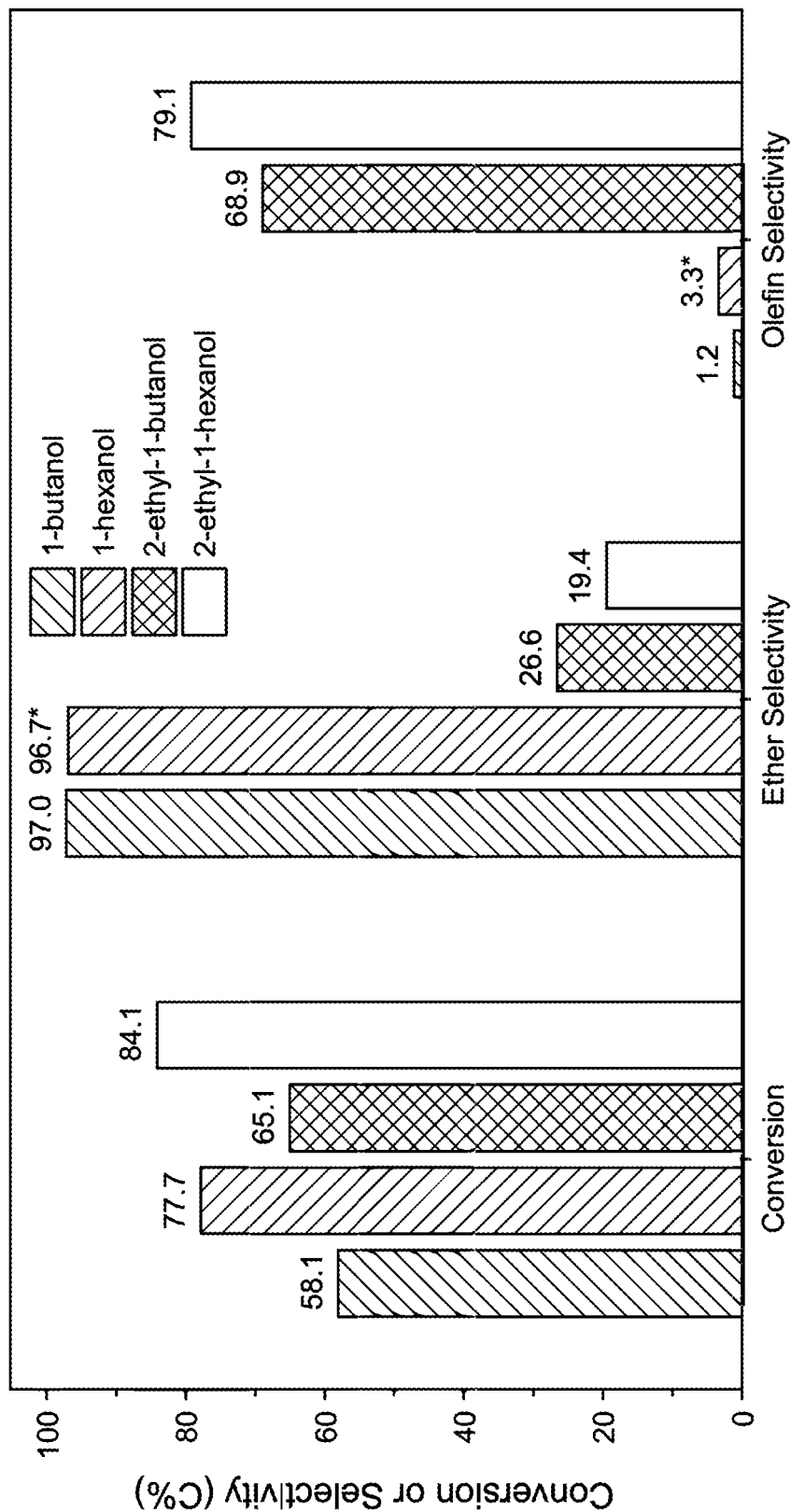
FIG. 7 is a bar chart showing alcohol dehydration conversions and selectivities.

Dehydrations were also performed on the primary branched alcohols 2-ethyl-1-butanol and 2-ethyl-1-hexanol. These alcohols are more selective to olefins than the linear alcohols. 2-ethyl-1-butanol was about 65% selective to 3-methylpentenes and 2-ethyl-1-hexanol about 75% selective to 3-methylheptenes. FIG. 7 illustrates the conversions and selectivities of the single-component alcohol feeds.

Figure 8:
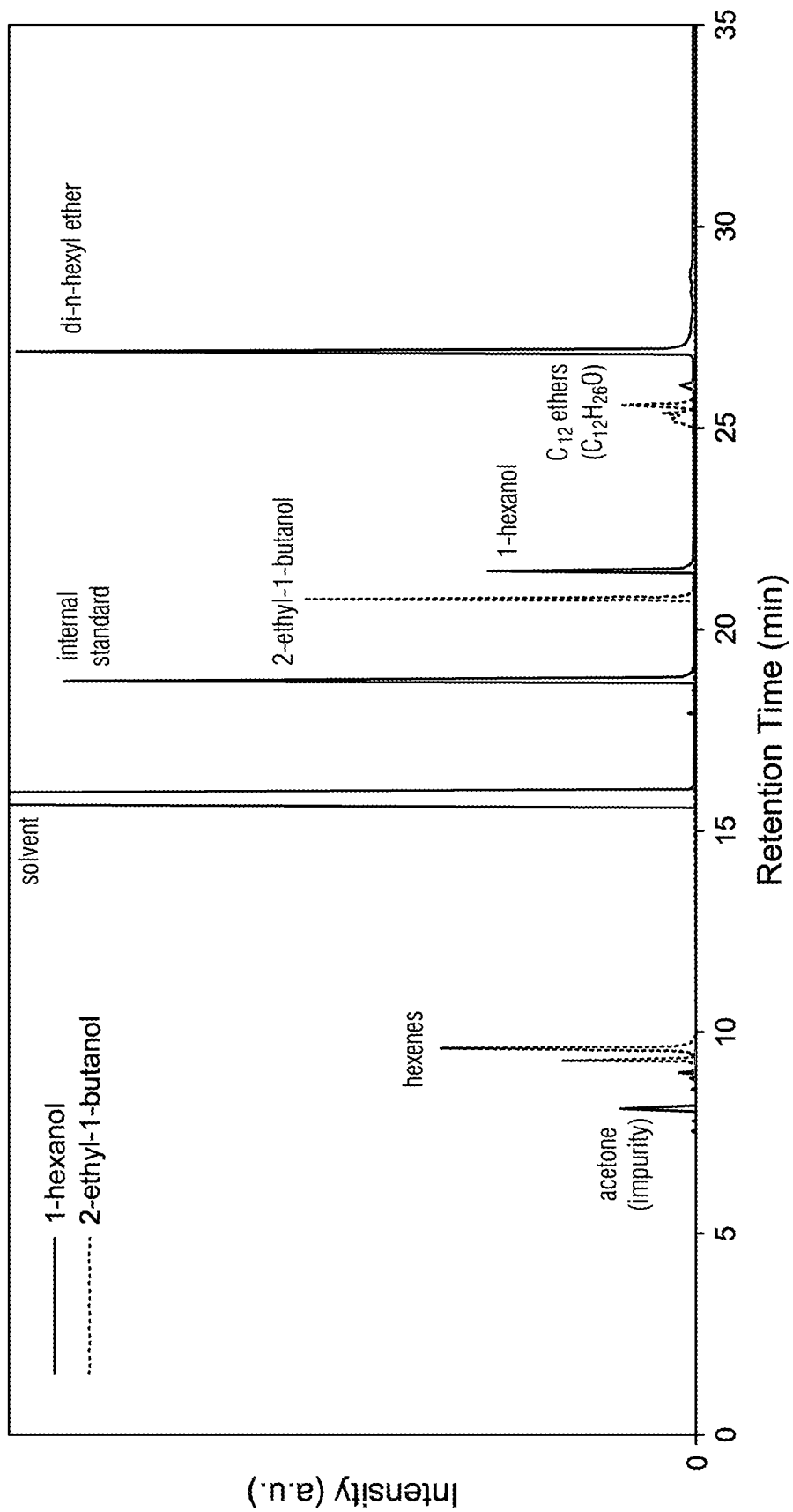
FIG. 8 illustrates the GCs of the dehydration products of 1-hexanol and 1-butyl-2-butanol.

FIG. 8 illustrates the superimposed GCs of the dehydration products of 1-hexanol and 2-ethyl-1-butanol. For 1-hexanol the major product observed was di-n-hexyl ether. For 2-ethyl-1-butanol, the products were hexenes and C12 ethers ($C_{12}H_{26}O$).

Example 5: Dehydration of Mixed Alcohol Feeds

Figure 9:
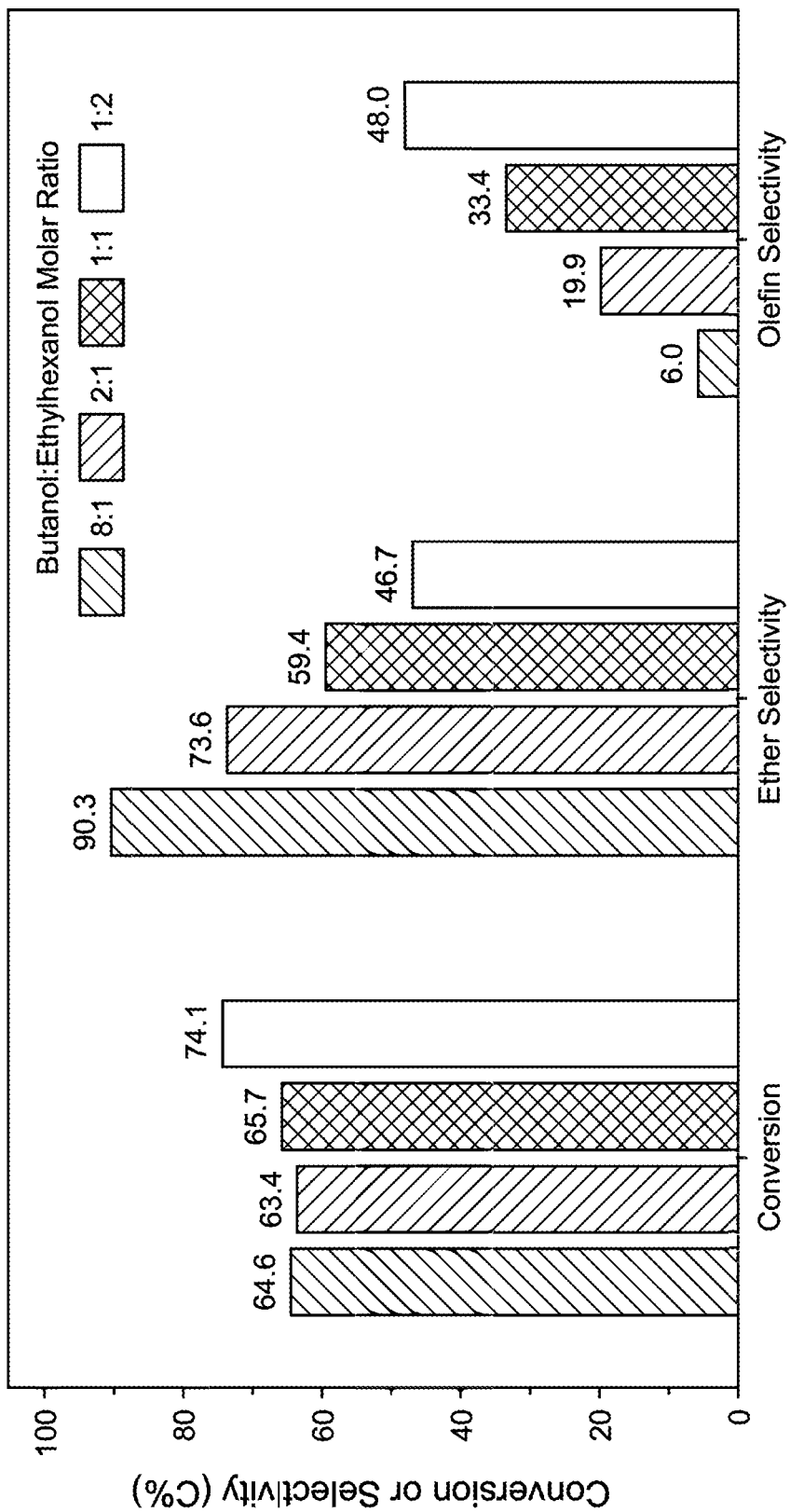
FIG. 9 is a bar chart showing mixed alcohol dehydration conversions and selectivities.

Dehydration of mixed alcohol feeds was undertaken as a model for Guerbet coupled products formed in Example 2. Mixtures of 1-butanol and 2-ethyl-1-hexanol were examined first with molar ratios of 8:1, 2:1, 1:1, and 1:2. FIG. 9 illustrates the conversions and selectivities from these dehydrations.

Feeds with higher 1-butanol contents show higher ether selectivities and lower olefin selectivities. No species other than light olefins and ethers were observed. The conversion of a 1:1 molar ratio of 1-butanol and 2-ethyl-1-hexanol led to an ether selectivity of 59% and an olefin selectivity of 33% at 66% feed conversion. The conversion of 1-butanol was 79% while that of 2-ethyl-1-hexanol was lower at 59%. The cross-etherification product 1-butoxy-2-ethylhexane was positively identified via gas chromatography-mass spectroscopy-electron ionization (GC-MS-EI), clearly showing that cross-etherification occurred between linear and branched alcohols.

Example 6: Dehydration of Mixed Alcohol Feeds

Model alcohol mixtures representative of ethanol coupled products were prepared and subjected to dehydration as per the method of Example 3. The compositions of the feed mixtures are shown in Table 6.

TABLE 6

| Composition | 1 | 2 | 3 | 4 |
|---|---|---|---|---|
| Linear:Branched ratio | 12.5 | 5.3 | 3.2 | 2.0 |
| Composition (mol %) | | | | |
| 1-butanol | 89.8 | 73.3 | 62.7 | 52.3 |
| 1-hexanol | 4.7 | 10.8 | 13.5 | 14.9 |
| 2-ethyl-1-butanol | 4.9 | 12.3 | 16.9 | 21.5 |
| 2-ethyl-1-hexanol | 0.5 | 3.5 | 6.9 | 11.3 |

Figure 10:
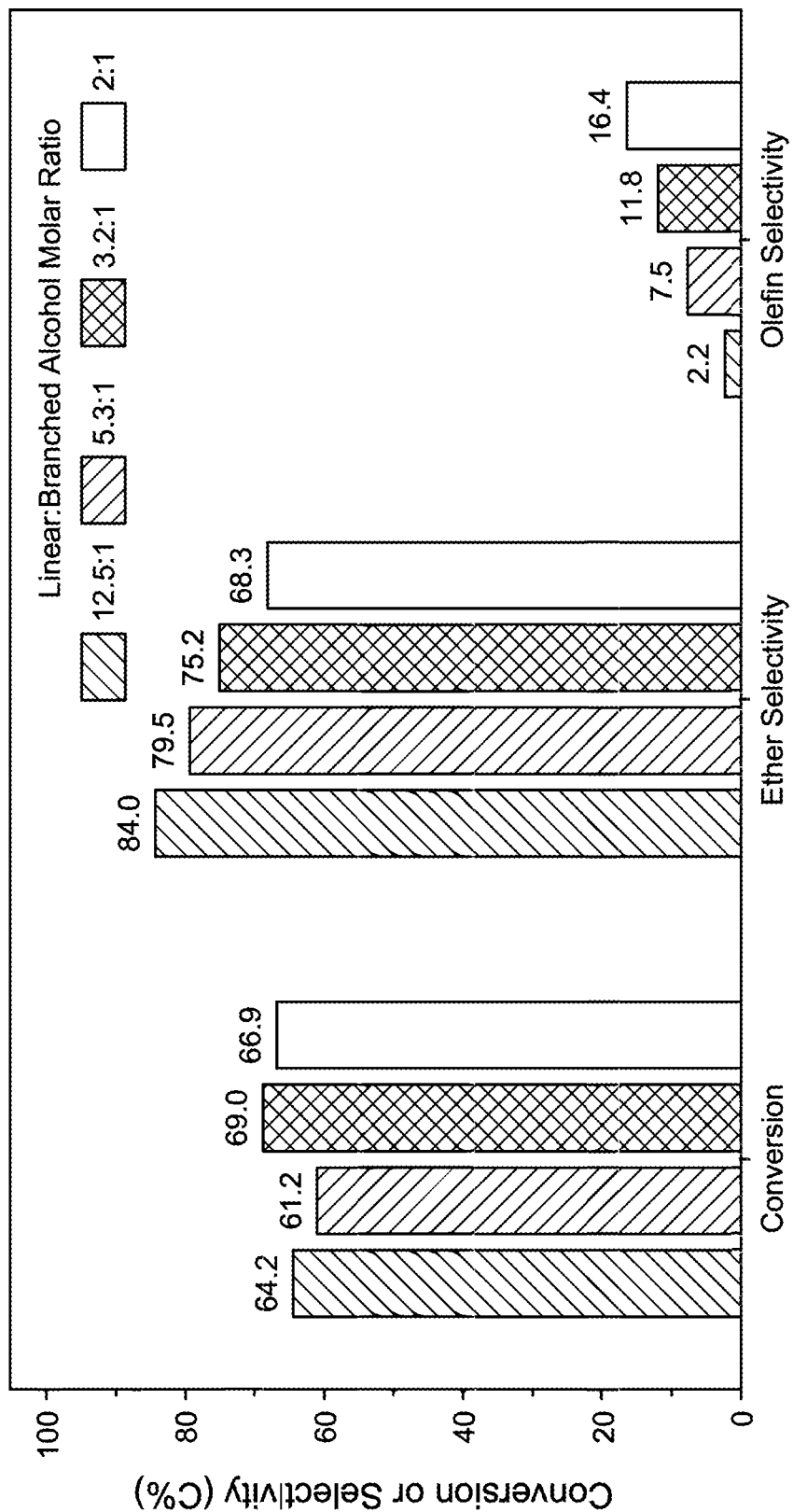
FIG. 10 is a bar chart showing mixed alcohol dehydration conversions and selectivities.

FIG. 10 illustrates the conversions and selectivities from these dehydrations. The mixtures reacted to 65.0-69.5% conversion with ether selectivities ranging from 65.0-81.8%. Cross-etherification was observed between the various alcohols with ethers positively identified based on molecular weight via GC-MS-FI. Approximately 15% of the products could not be identified. As in the etherification of butanol-ethylhexanol mixtures, ether and olefin selectivities were directly correlated with the linear:branched alcohol feed ratio, though ether selectivities are slightly lower than with the two-component feed. This implies that performing Guerbet condensation at higher conversions where the linear:branched alcohol ratio is lower will result in lower ether selectivities. The olefins were almost entirely 3-methylpentenes and 3-methylheptenes derived from the branched alcohols.

Example 7: Combined Alcohol Coupling and Dehydration

Guerbet coupling was performed in a stainless-steel fixed-bed reactor (40 cm long, 0.95 cm outer diameter) packed with 6.0 g of calcium hydroxyapatite (HAP, Acros Organics) pelletized and sieved to a particle size of 250-354 μm. Prior to reaction, HAP was calcined in 65 mL min$^{-1}$ air at 500° C. (2° C. min$^{-1}$, 2 h hold). Alcohols were fed (10-50 μL min$^{-1}$) with a syringe pump (Teledyne ISCO) concurrently with $H_2$ gas (50-200 mL min-1) at atmospheric pressure in the downflow configuration through a preheated evaporation region maintained at >200° C. prior to entering the reactor. Coupling was carried out at 325° C., 520 s $kg_{HAP}$ $mol_{alcohol}^{-1}$, 8 kPa alcohol, 93 kPa $H_2$.

Ethanol coupling was performed to produce C4+ alcohols. As the water by-product inhibits the following dehydration step it was removed from the product alcohols using molecular sieves. In this way, water concentration was reduced from 15 wt. % to less than 0.5 wt. %. Unreacted ethanol was also removed by distillation. The major components after ethanol removal were 1-butanol (51.8 wt. %), 2-ethyl-1-butanol (13.6 wt. %), 1-hexanol (12.5 wt. %), and 2-ethyl-1-hexanol (4.1 wt. %) with the remainder comprising other alcohols (4.7 wt. %) and species not detected via GC (13.2 wt. %). 79.9 mol. % of the alcohols in the feed were linear.

The mixture of alcohols was subsequently dehydrated over Amberlyst™ 70 to ethers with 73.5% alcohol conversion, 71.6% ether selectivity, and 10.2% olefin selectivity.

CERTAIN EMBODIMENTS

Certain embodiments of processes according to the present disclosure are presented in the following paragraphs.

Embodiment 1 provides a process for producing ethers and olefins from primary alcohols, said process comprising:
(a) contacting a feed comprising primary alcohols with a first catalyst in a first reactor under conditions effective to produce an effluent comprising higher alcohols; and
(b) contacting at least some of the higher alcohols produced in (a) with a second catalyst in a second reactor under conditions effective to dehydrate at least some of the higher alcohols to ethers and olefins.

Embodiment 2 provides a process according to embodiment 1, wherein the primary alcohols comprise one or more C2 to C5 alcohols.

Embodiment 3 provides a process according to embodiment 1 or embodiment 2, wherein the primary alcohols in (a) comprise one or more of ethanol and 1-butanol.

Embodiment 4 provides a process according to any one of embodiments 1 to 3, wherein the contacting in step (a) is performed in the presence of one or more of hydrogen and inert gas.

Embodiment 5 provides a process according to any one of embodiments 1 to 4, wherein the higher alcohols produced in step (a) comprise one or more C4+ alcohols.

Embodiment 6 provides a process according to any one of embodiments 1 to 5, wherein step (a) is performed at a temperature from about 250° C. to about 370° C., preferably from about 280° C. to about 350° C.

Embodiment 7 provides a process according to any one of embodiments 1 to 6, wherein step (a) is performed at a pressure from about 15 psi (0.1 MPa) to about 1000 psi (6.9 MPa), or from about 100 psi (0.69 MPa) to about 1000 psi (6.9 MPa), or from about 200 psi (1.38 MPa) to about 500 psi (3.45 MPa).

Embodiment 8 provides a process according to any one of embodiments 1 to 7, wherein the partial pressure of hydrogen is less than 100 psi (0.69 MPa), or less than 90 psi (0.62 MPa), or less than 80 psi (0.55 MPa) or less than 70 psi (0.48 MPa), or less than 60 psi (0.41 MPa).

Embodiment 9 provides a process according to any one of embodiments 1 to 8, wherein the first catalyst is a heterogeneous catalyst comprising one or more Group A oxides, said Group A oxides being oxides of Mg, Ca, Zn, Mn, Sr, Si and Zr; one or more Group B oxides, said Group B oxides being one or more oxides of Al, La, Ga, Ce, Fe, Sc, Cr, P and V; and combinations of both Group A and Group B oxides, and, optionally, one or more of Cu, Ni, Pt, Pd, Rh, Co, Cs and Rb.

Embodiment 10 provides a process according to any one of embodiments 1 to 8, wherein the first catalyst is a heterogeneous catalyst comprising one or more oxides of Mg, Ca, Zn, Sr, Al and Ce.

Embodiment 11 provides a process according to any one of embodiments 1 to 8, wherein the first catalyst is a heterogeneous catalyst comprising one or more oxides of Mg, Ca and Zn, one or more oxides of Al, La, Ga, Ce, Fe and Cr, and one or more of Cu, Ni, Pt, Pd, Rh and Co.

Embodiment 12 provides a process according to any one of embodiments 1 to 8, wherein the first catalyst is a heterogeneous catalyst comprising one or more oxides of Mg, Ca and Sr, one or more of P and V, and, optionally, one or more of Cu, Ni, Pt, Pd, Rh, and Co.

Embodiment 13 provides a process according to any one of embodiments 1 to 8, wherein the first catalyst is a heterogeneous catalyst comprising Al and Si metal oxides and one or more of Cs and Rb.

Embodiment 14 provides a process according to embodiment 9, wherein the weight percent of the one or more of Cu, Ni, Pt, Pd, Rh and Co is up to about 10 wt. %, or from about 0.01 wt. % to about 9 wt. %, or from about 0.01 wt. % to about 8 wt. %, or from about 0.01 wt. % to about 7 wt. %, or from about 0.01 wt. % to about 6 wt. %, or from about 0.01 wt. % to about 5 wt. %, or from about 0.01 wt. % to about 4 wt. %, or from about 0.01 wt. % to about 3 wt. %, or from about 0.01 wt. % to about 2 wt. %, or from about 0.01 wt. % to about 1 wt. %, or from about 0.01 wt. % to about 0.5 wt. %, or from about 0.01 wt. % to about 0.4 wt. %, or from about 0.01 wt. % to about 0.3 wt. %, or from about 0.01 wt. % to about 0.2 wt. %, or from about 0.01 wt. % to about 0.1 wt. %, based on the total weight of the catalyst.

Embodiment 15 provides a process according to embodiment 9, wherein the first catalyst comprises Mg and Al oxides and Cu and the weight percent of Cu is preferably 0.05 wt. % to 1.0 wt. %, or 0.05 wt. % to 0.5 wt. %, or 0.05 wt. % to 0.2 wt. %, based on the total weight of the catalyst.

Embodiment 16 provides a process according to any one of embodiments 1 to 15, wherein the first catalyst is reduced prior to use.

Embodiment 17 provides a process according to any one of embodiments 1 to 16, wherein the selectivity to alcohols in step (a) is at least about 45%, or at least about 50%, or at least about 55%, or at least about 60%, or at least about 65%, or at least about 70%, or at least about 75%, or at least about 80%.

Embodiment 18 provides a process according to any one of embodiments 1 to 17, wherein the selectivity to primary linear alcohols in step (a), based on total alcohols formed, is at least about 80%, or at least about 85%, or at least about 90%, or at least about 95%, or at least about 96%, or at least about 97%, or at least about 98%, or at least about 99%.

Embodiment 19 provides a process according to any one of embodiments 1 to 18, wherein the selectivity to primary branched alcohols in step (a), based on total alcohols formed, is less than about 20%, or less than about 15%, or less than about 10%, or less than about 5%, or less than about 4%, or less than about 3%, or less than about 2%, or less than about 1%.

Embodiment 20 provides a process according to any one of embodiments 1 to 19, wherein the effluent from step (a) further comprises one or more olefins.

Embodiment 21 provides a process according to embodiment 20, wherein the selectivity to olefins in step (a) is less than about 20%, or less than about 15%, or less than about 10%, or less than about 5%.

Embodiment 22 provides a process according to any one of embodiments 1 to 21, wherein the effluent from step (a) further comprises one or more esters.

Embodiment 23 provides a process according to embodiment 22, wherein the selectivity to esters in step (a) is less than about 30%, or less than about 25%, or less than about 20%, or less than about 15%, or less than about 10%, or less than about 5%.

Embodiment 24 provides a process according to any one of embodiments 1 to 23, wherein the effluent from step (a) further comprises one or more ethers.

Embodiment 25 provides a process according to embodiment 24, wherein the selectivity to ethers in step (a) is less than about 20%, or less than about 15%, or less than about 10%, or less than about 5%.

Embodiment 26 provides a process according to any one of embodiments 1 to 25, wherein the effluent from step (a) further comprises one or more aldehydes and/or ketones.

Embodiment 27 provides a process according embodiment 26, wherein the selectivity to aldehydes and ketones in step (a) is less than about 20%, or less than about 15%, or less than about 10%, or less than about 5%.

Embodiment 28 provides a process according to any one of embodiments 1 to 27, wherein step (b) is performed at a temperature from about 100° C. to about 180° C.

Embodiment 29 provides a process according to any one of embodiments 1 to 28, wherein the second catalyst is a solid acid catalyst comprising one or more of acidic resins, alumina and aluminosilicates, heteropoly acids, and tungsten and molybdenum functionalized oxides.

Embodiment 30 provides a process according to any one of embodiments 1 to 29, wherein the ethers produced in step (b) comprise one or more C8-C24 ethers.

Embodiment 31 provides a process according to any one of embodiments 1 to 30, wherein the olefins produced in step (b) comprise one or more C6-C14 olefins.

Embodiment 32 provides a process for producing ethers and olefins from primary alcohols, said process comprising:
(a) contacting a feed comprising primary alcohols with a first catalyst in a first reactor under conditions effective to produce an effluent comprising higher alcohols and olefins;
(b) separating the effluent from step (a) into a first stream rich in olefins and one or more second streams rich in alcohols, wherein the one or more second streams rich in alcohols comprise a first stream rich in C2-C4 alcohols and a second stream rich in C4+ alcohols;
(c) recycling at least a portion of the first stream rich in C2-C4 alcohols to step (a);
(d) contacting at least a portion of the second stream rich in C4+ alcohols with a second catalyst in a second reactor under conditions effective to dehydrate at least some of the C4+ alcohols to ethers and olefins; and
(e) separating the ethers and olefins produced in step (d) into a second stream rich in olefins, a stream rich in ethers, and a stream rich in alcohols.

Embodiment 33 provides a process according to embodiment 32, wherein the primary alcohols comprise one or more C2 to C5 alcohols.

Embodiment 34 provides a process according to embodiment 32 or embodiment 33, wherein the primary alcohols in (a) comprise one or more of ethanol and 1-butanol.

Embodiment 35 provides a process according to any one of embodiments 32 to 34, wherein the contacting in step (a) is performed in the presence of one or more of hydrogen and inert gas.

Embodiment 36 provides a process according to any one of embodiments 32 to 35, wherein the higher alcohols produced in step (a) comprise one or more C4+ alcohols.

Embodiment 37 provides a process according to any one of embodiments 32 to 36 wherein step (a) is performed at a temperature from about 250° C. to about 370° C., preferably from about 280° C. to about 350° C.

Embodiment 38 provides a process according to any one of embodiments 32 to 37, wherein step (a) is performed at a pressure from about 15 psi (0.1 MPa) to about 1000 psi (6.9 MPa), or from about 100 psi (0.69 MPa) to about 1000 psi (6.9 MPa), or from about 200 psi (1.38 MPa) to about 500 psi (3.45 MPa).

Embodiment 39 provides a process according to any one of embodiments 32 to 38, wherein the partial pressure of hydrogen is less than 100 psi (0.69 MPa), or less than 90 psi (0.62 MPa), or less than 80 psi (0.55 MPa) or less than 70 psi (0.48 MPa), or less than 60 psi (0.41 MPa).

Embodiment 40 provides a process according to any one of embodiments 32 to 39, wherein the first catalyst is a heterogeneous catalyst comprising one or more Group A oxides, said Group A oxides being oxides of Mg, Ca, Zn, Mn, Sr, Si and Zr; one or more Group B oxides, said Group B oxides being one or more oxides of Al, La, Ga, Ce, Fe, Sc, Cr, P and V; and combinations of both Group A and Group B oxides, and, optionally, one or more of Cu, Ni, Pt, Pd, Rh, Co, Cs and Rb.

Embodiment 41 provides a process according to any one of embodiments 32 to 39, wherein the first catalyst is a heterogeneous catalyst comprising one or more oxides of Mg, Ca, Zn, Sr, Al and Ce.

Embodiment 42 provides a process according to any one of embodiments 32 to 39, wherein the first catalyst is a heterogeneous catalyst comprising one or more oxides of Mg, Ca and Zn, one or more oxides of Al, La, Ga, Ce, Fe and Cr, and one or more of Cu, Ni, Pt, Pd, Rh and Co.

Embodiment 43 provides a process according to any one of embodiments 32 to 39, wherein the first catalyst is a heterogeneous catalyst comprising one or more oxides of Mg, Ca and Sr, one or more of P and V, and, optionally, one or more of Cu, Ni, Pt, Pd, Rh and Co.

Embodiment 44 provides a process according to any one of embodiments 32 to 39, wherein the first catalyst is a heterogeneous catalyst comprising Al and Si metal oxides and one or more of Cs and Rb.

Embodiment 45 provides a process according to embodiment 40, wherein the weight percent of the one or more of Cu, Ni, Pt, Pd, Rh and Co is up to about 10 wt. %, or from about 0.01 wt. % to about 9 wt. %, or from about 0.01 wt. % to about 8 wt. %, or from about 0.01 wt. % to about 7 wt. %, or from about 0.01 wt. % to about 6 wt. %, or from about 0.01 wt. % to about 5 wt. %, or from about 0.01 wt. % to about 4 wt. %, or from about 0.01 wt. % to about 3 wt. %, or from about 0.01 wt. % to about 2 wt. %, or from about 0.01 wt. % to about 1 wt. %, or from about 0.01 wt. % to about 0.5 wt. %, or from about 0.01 wt. % to about 0.4 wt. %, or from about 0.01 wt. % to about 0.3 wt. %, or from about 0.01 wt. % to about 0.2 wt. %, or from about 0.01 wt. % to about 0.1 wt. %, based on the total weight of the catalyst.

Embodiment 46 provides a process according to embodiment 40, wherein the first catalyst comprises Mg and Al oxides and Cu and the weight percent of Cu is preferably 0.05 wt. % to 1.0 wt. %, or 0.05 wt. % to 0.5 wt. %, or 0.05 wt. % to 0.2 wt. %, based on the total weight of the catalyst.

Embodiment 47 provides a process according to any one of embodiments 40 to 46, wherein the first catalyst is reduced prior to use.

Embodiment 48 provides a process according to any one of embodiments 32 to 47, wherein the selectivity to alcohols in step (a) is at least about 45%, or at least about 50%, or at least about 55%, or at least about 60%, or at least about 65%, or at least about 70%, or at least about 75%, or at least about 80%.

Embodiment 49 provides a process according to any one of embodiments 32 to 48, wherein the selectivity to primary linear alcohols in step (a), based on total alcohols formed, is at least about 80%, or at least about 85%, or at least about 90%, or at least about 95%, or at least about 96%, or at least about 97%, or at least about 98%, or at least about 99%.

Embodiment 50 provides a process according to any one of embodiments 32 to 49, wherein the selectivity to primary branched alcohols in step (a), based on total alcohols formed, is less than about 20%, or less than about 15%, or less than about 10%, or less than about 5%, or less than about 4%, or less than about 3%, or less than about 2%, or less than about 1%.

Embodiment 51 provides a process according to any one of embodiments 32 to 50, wherein the selectivity to olefins in step (a) is less than about 20%, or less than about 15%, or less than about 10%, or less than about 5%.

Embodiment 52 provides a process according to any one of embodiments 32 to 51, wherein the effluent from step (a) further comprises one or more esters.

Embodiment 53 provides a process according to embodiment 52, wherein the selectivity to esters in step (a) is less than about 30%, or less than about 25%, or less than about 20%, or less than about 15%, or less than about 10% or less than about 5%.

Embodiment 54 provides a process according to any one of embodiments 32 to 53, wherein the effluent from step (a) further comprises one or more ethers.

Embodiment 55 provides a process according to embodiment 54, wherein the selectivity to ethers in step (a) is less than about 20%, or less than about 15%, or less than about 10%, or less than about 5%.

Embodiment 56 provides a process according to any one of embodiments 32 to 55, wherein the effluent from step (a) further comprises one or more aldehydes and ketones.

Embodiment 57 provides a process according to embodiment 56, wherein the selectivity to aldehydes and ketones in step (a) is less than about 20%, or less than about 15%, or less than about 10%, or less than about 5%.

Embodiment 58 provides a process according to any one of embodiments 32 to 57, wherein step (d) is performed at a temperature from about 100° C. to about 180° C.

Embodiment 59 provides a process according to any one of embodiments 32 to 58, wherein the second catalyst is a solid acid catalyst comprising one or more of acidic resins, alumina and aluminosilicates, heteropoly acids, and tungsten and molybdenum functionalized oxides.

Embodiment 60 provides a process according to any one of embodiments 32 to 59, wherein the ethers produced in step (d) comprise one or more C8-C24 ethers.

Embodiment 61 provides a process according to any one of embodiments 32 to 60, wherein the olefins produced in step (d) comprise one or more C6-C14 olefins.

Embodiment 62 provides a process according to any one of embodiments 32 to 61, wherein the process further comprises the step of combining at least a portion of the first stream rich in olefins produced in step (b) with at least a portion of the second stream rich in olefins produced in step (e).

Embodiment 63 provides a process according to any one of embodiments 32 to 62, wherein the first stream rich in olefins produced in step (b) comprises C2-C4 olefins.

Embodiment 64 provides a process according to any one of embodiments 32 to 63, wherein the process further comprises the step of recycling at least a portion of the stream rich in alcohols produced in step (e) to step (d).

Embodiment 65 provides a process according to any one of embodiments 32 to 64, wherein the stream rich in ethers produced in step (e) comprises one or more C8-C16+ ethers.

Embodiment 66 provides a process according to any one of embodiments 32 to 65, wherein the second stream rich in olefins produced in step (e) comprises one or more C6+ olefins.

Embodiment 67 provides a process according to any one of embodiments 32 to 66, wherein at least a portion of any one or more of the first stream rich in olefins, the second stream rich in olefins, and the combined streams of olefins are oligomerized to higher olefins in the presence of a catalyst comprising acidic sites.

Embodiment 68 provides a process according to embodiment 67, wherein the catalyst comprising acid sites further comprises a transition metal, for example cobalt or nickel.

Embodiment 69 provides a process according to embodiment 67 or embodiment 68, wherein the higher olefins comprise C8-C16+ olefins.

Embodiment 70 provides a process according to any one of embodiments 67 to 69, wherein the higher olefins are hydrotreated in the presence of a transition metal catalyst to paraffins.

Embodiment 71 provides a process according to embodiment 70, wherein the paraffins comprise C8-C16+ paraffins.

The contents of all references and published patents and patent applications cited throughout the application are hereby incorporated by reference.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the reactants may be varied to optimize the desired effects, additional reactants may be added, and/or similar reactants may be substituted for one or more of the reactants described. Additional advantageous features and functionalities associated with the processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

The invention claimed is:

1. A process for producing ethers and olefins from primary alcohols, said process comprising:
   (a) contacting a feed comprising primary alcohols with a first catalyst in a first reactor under conditions effective to produce an effluent comprising one or more C4+ alcohols, the primary alcohols comprising ethanol and 1-butanol, the first catalyst comprising an oxide of Mg, one or more oxides of Al, La, Ga, Ce, Fe, Sc, Cr, P and V, and one or more of Cu, Ni, Pt, Pd, Rh, Co, Cs and Rb;
   (b) separating the effluent from step (a) to form one or more streams rich in alcohols, wherein the one or more streams rich in alcohols comprise a first stream comprising C2-C4 alcohols and a second stream rich in C4+ alcohols;
   (c) recycling at least a portion of the first stream comprising C2-C4 alcohols to step (a); and
   (d) contacting at least a portion of the second stream comprising C4+ alcohols with a second catalyst in a second reactor under conditions effective to dehydrate at least a portion of the C4+ alcohols to form a dehydration product comprising olefins and C8-C24 ethers.

2. The process of claim 1, wherein the primary alcohols comprise one or more C2 to C5 alcohols.

3. The process of claim 1, wherein the primary alcohols in (a) further comprise ethanol.

4. The process of claim 1, wherein the contacting in step (a) is performed in the presence of one or more of hydrogen and inert gas.

5. The process of claim 1, wherein step (a) is performed at a temperature from about 250° C to about 370° C.

6. The process of claim 1, wherein step (a) is performed at a pressure from about 15 psi (0.1 MPa) to about 1000 psi (6.9 MPa).

7. The process of claim 4, wherein the partial pressure of hydrogen is less than 100 psi (0.69 MPa).

8. The process of claim 1, wherein the first catalyst further comprises one or more oxides of Ca, Zn, Sr, Al and Ce.

9. The process of claim 1, wherein the first catalyst comprises one or more oxides of Al, La, Ga, Ce, Fe and Cr, and one or more of Cu, Ni, Pt, Pd, Rh and Co.

10. The process of claim 1, wherein the first catalyst further comprises one or more of P and V.

11. The process of claim 1, wherein the weight percent of the one or more of Cu, Ni, Pt, Pd, Rh, and Co is up to about 10 wt. %, based on the total weight of the catalyst.

12. The process of claim 1, wherein the first catalyst comprises Mg and Al oxides and Cu and the weight percent of Cu is 0.05 wt. % to 1.0 wt. %, based on the total weight of the catalyst.

13. The process of claim 1, wherein the first catalyst is reduced prior to use.

14. The process of claim 1, wherein the selectivity to alcohols in step (a) is at least about 45%.

15. The process of claim 1, wherein the selectivity to primary branched alcohols in step (a), based on total alcohols formed, is less than about 15%.

16. The process of claim 1, wherein the effluent from step (a) further comprises one or more olefins.

17. The process of claim 16, wherein the selectivity to olefins in step (a) is less than about 20%.

18. The process of claim 1, wherein the effluent from step (a) further comprises one or more esters.

19. The process of claim 18, wherein the selectivity to esters in step (a) is less than about 15%.

20. The process of claim 1, wherein the effluent from step (a) further comprises one or more ethers.

21. The process of claim 20, wherein the selectivity to ethers in step (a) is less than about 20%.

22. The process of claim 1, wherein the effluent from step (a) further comprises one or more aldehydes and/or ketones.

23. The process of claim 22, wherein the selectivity to aldehydes and ketones in step (a) is less than about 10%.

24. The process of claim 1, wherein step (b) is performed at a temperature from about 100° C. to about 180° C.

25. The process of claim 1, wherein the second catalyst is a solid acid catalyst comprising one or more of acidic resins, alumina and aluminosilicates, heteropoly acids, and tungsten and molybdenum functionalized oxides.